United States Patent
Tabash et al.

(10) Patent No.: US 8,207,149 B2
(45) Date of Patent: Jun. 26, 2012

(54) METHOD FOR TREATING SECONDARY HYPERPARATHYROIDISM IN CKD

(75) Inventors: Samir P. Tabash, Whitby (CA); Jay A. White, Newmarket (CA); Charles W. Bishop, Mount Horeb, WI (US); Sammy A. Agudoawu, Mississauga (CA); Eric J. Messner, Lake Forest, IL (US); P. Martin Petkovich, Kingston (CA)

(73) Assignees: Cytochroma, Inc., Markham (CA); Proventiv Therapeutics, LLC, Bannockburn, IL (US)

( * ) Notice: Subject to any disclaimer, the term of this patent is extended or adjusted under 35 U.S.C. 154(b) by 0 days.

(21) Appl. No.: 13/244,945

(22) Filed: Sep. 26, 2011

(65) Prior Publication Data

US 2012/0015916 A1    Jan. 19, 2012

Related U.S. Application Data

(63) Continuation of application No. 12/109,983, filed on Apr. 25, 2008.

(60) Provisional application No. 60/913,853, filed on Apr. 25, 2007.

(51) Int. Cl.
*A61K 31/593* (2006.01)
*A61K 31/592* (2006.01)
*A61P 5/18* (2006.01)

(52) U.S. Cl. ....................................................... 514/167
(58) Field of Classification Search .................... 514/167
See application file for complete search history.

(56) References Cited

U.S. PATENT DOCUMENTS

| | | |
|---|---|---|
| 3,565,924 A | 2/1971 | DeLuca et al. |
| 3,880,894 A | 4/1975 | De Luca et al. |
| 4,004,003 A | 1/1977 | Babcock et al. |
| 4,230,701 A | 10/1980 | Holick et al. |
| 4,335,120 A | 6/1982 | Holick et al. |
| 4,555,364 A | 11/1985 | DeLuca et al. |
| 4,668,517 A | 5/1987 | Weber et al. |
| 4,684,524 A | 8/1987 | Eckenhoff et al. |
| 4,695,591 A | 9/1987 | Hanna et al. |
| 4,721,613 A | 1/1988 | Urquhart et al. |
| 4,729,895 A | 3/1988 | Makino et al. |
| 4,755,544 A | 7/1988 | Makino et al. |
| 5,026,559 A | 6/1991 | Eichel et al. |
| 5,160,742 A | 11/1992 | Mazer et al. |
| 5,328,903 A | 7/1994 | Ishii et al. |
| 5,403,831 A | 4/1995 | DeLuca et al. |
| 5,487,900 A | 1/1996 | Itoh et al. |
| 5,529,991 A | 6/1996 | Knutson et al. |
| 5,593,690 A | 1/1997 | Akiyama et al. |
| 5,602,116 A | 2/1997 | Knutson et al. |
| 5,614,513 A | 3/1997 | Knutson et al. |
| 5,622,941 A | 4/1997 | Knutson et al. |
| 5,693,615 A | 12/1997 | Stone |
| 5,707,980 A | 1/1998 | Knutson et al. |
| 5,795,882 A | 8/1998 | Bishop et al. |
| 5,861,386 A | 1/1999 | Knutson et al. |
| 5,869,473 A | 2/1999 | Knutson et al. |
| 6,051,567 A | 4/2000 | Abrahamson et al. |
| 6,133,250 A | 10/2000 | Knutson et al. |
| 6,139,875 A | 10/2000 | Adams et al. |
| 6,147,064 A | 11/2000 | Knutson et al. |
| 6,150,346 A | 11/2000 | Knutson et al. |
| 6,190,591 B1 | 2/2001 | van Lengerich |
| 6,190,695 B1 | 2/2001 | Hoshino et al. |
| 6,228,849 B1 | 5/2001 | Thys-Jacobs |
| 6,265,392 B1 | 7/2001 | Abrahamson et al. |
| 6,274,169 B1 | 8/2001 | Abrahamson et al. |
| 6,342,249 B1 | 1/2002 | Wong et al. |
| 6,376,479 B1 | 4/2002 | Knutson et al. |
| 6,380,408 B1 | 4/2002 | Posner et al. |
| 6,432,936 B1 | 8/2002 | DeLuca et al. |
| 6,596,314 B2 | 7/2003 | Wong et al. |
| 6,903,083 B2 | 6/2005 | Knutson et al. |
| 6,923,988 B2 | 8/2005 | Patel et al. |
| 6,929,803 B2 | 8/2005 | Wong et al. |
| 6,982,258 B2 | 1/2006 | Posner et al. |
| 7,101,865 B2 | 9/2006 | Posner et al. |
| 2002/0183288 A1 | 12/2002 | Mazess et al. |
| 2004/0043971 A1 | 3/2004 | Mazess et al. |
| 2004/0101554 A1 | 5/2004 | Kirschner et al. |
| 2005/0101576 A1 | 5/2005 | Whitehouse et al. |
| 2005/0124591 A1 | 6/2005 | Tian et al. |
| 2005/0148557 A1 | 7/2005 | Tian et al. |
| 2006/0193877 A1 | 8/2006 | Tengler et al. |
| 2009/0176748 A1 | 7/2009 | Tabash et al. |
| 2009/0311316 A1 | 12/2009 | Bishop et al. |

FOREIGN PATENT DOCUMENTS

CA    2241205 A1    7/1997

(Continued)

OTHER PUBLICATIONS

Brown (Vitamin D analogues for secondary hyperparathyroidism, Nephrol Dial Transplant (2002), 17 [Suppl 10], pp. 10-19).*
Halloran (Plasma vitamin D metabolite concentration in chronic renal failure; effect of oral administration of 25-hydroxyvitamin D3, J. clin endocrinol Metabolism, Dec. 1984 59(6) pp. 1063-1069 (abstract only).*
Zerwekh et al (Extra-renal production of 24,25-dihydroxyvitamin D in chronic renal failure during 25 hydroxyvitamin D3 therapy, Kidney International, vol. 23, (1983).*

(Continued)

*Primary Examiner* — Brandon Fetterolf
*Assistant Examiner* — Kathrien Cruz
(74) *Attorney, Agent, or Firm* — Marshall, Gerstein & Borun LLP

(57) ABSTRACT

A stable, controlled release formulation for oral dosing of vitamin D compounds is disclosed. The formulation is prepared by incorporating one or more vitamin D compounds into a solid or semi-solid mixture of waxy materials. Oral dosage forms can be prepared by melt-blending the components described herein and filling gelatin capsules with the formulation.

11 Claims, 14 Drawing Sheets

FOREIGN PATENT DOCUMENTS

| | | |
|---|---|---|
| EP | 0 227 836 A1 | 7/1987 |
| EP | 0 508 756 A1 | 10/1992 |
| JP | 04-208225 A | 7/1992 |
| JP | 07-242550 A | 9/1995 |
| JP | 08-092098 A | 4/1996 |
| JP | 10-158171 A | 6/1998 |
| JP | 2004-175750 A | 6/2004 |
| WO | WO-91/12807 A1 | 9/1991 |
| WO | WO-91/16899 A1 | 11/1991 |
| WO | WO-94/00128 A1 | 1/1994 |
| WO | WO-96/00074 A1 | 1/1996 |
| WO | WO-96/31215 A1 | 10/1996 |
| WO | WO-97/11053 A1 | 3/1997 |
| WO | WO-98/18610 A1 | 5/1998 |
| WO | WO-99/11272 A1 | 3/1999 |
| WO | WO-00/21504 A1 | 4/2000 |
| WO | WO-00/35419 A2 | 6/2000 |
| WO | WO-03/039521 A1 | 5/2003 |
| WO | WO-03/039572 A1 | 5/2003 |
| WO | WO-03/047595 A1 | 6/2003 |
| WO | WO-2004/028515 A1 | 4/2004 |
| WO | WO-2004/058235 A2 | 7/2004 |
| WO | WO-2004/080467 A2 | 9/2004 |
| WO | WO-2005/011652 A2 | 2/2005 |
| WO | WO-2005/123120 A1 | 12/2005 |
| WO | WO-2007/047327 A2 | 4/2007 |
| WO | WO-2007/092755 A2 | 8/2007 |
| WO | WO-2008/008608 A2 | 1/2008 |
| WO | WO-2008/134523 A1 | 11/2008 |
| WO | WO-2010/011906 A1 | 1/2010 |

OTHER PUBLICATIONS

Coyne et al., "Paricalcitol Capsule for the Treatment of Secondary Hyperparathyroidism in Stages 3 and 4 CKD," *American Journal of Kidney Diseases*, 47(2):263-276 (2006).

Holick, "Vitamin D Status: Measurement, Interpretation and Clinical Application," *Ann Epidemiol*, 19(2):73-78 2009.

"K/DOQI Clinical Practice Guidelines for Bone Metabolism and Disease in Chronic Kidney Disease," National Kidney Foundation, *Am. J. Kidney Dis.*, 42 (Supplement 3):1-202 (2003).

Al-Aly, Z., "Changes in Serum 25-Hydroxyvitamin D and Plasma Intact PTH Levels Following Treatment with Ergocalciferol in Patients With CKD," Am. J. Kid. Dis., 50(1):59-68 (2007).

Andress, "Vitamin D in chronic kidney disease: A systematic role for selective vitamin D receptor activation," *Kidney Int.*, 69:33-43 (2006).

Arekat et al., "Dramatic Improvement of BMD Following Vitamin D Therapy in a Bone Marrow Transplant Recipient," *J. Clin. Densitometry*, 5:267-271 (2002).

Armas et al., "Vitamin $D_2$ is Much Less Effective than Vitamin $D_3$ in Humans," *J. Clin. Endocrinol. Metab.*, 89:5387-5391 (2004).

Bagnis et al., "Biochemical and Hormonal Short-Term Effects of 25-hydroxyvitamin D3 in Patients on Continuous Peritoneal Dialysis," *Ital. J. Mineral Electrolyte Metab.*, 12:73-76 (1998).

Bailie et al. "Comparative Review of the Pharmacokinetics of Vitamin D Analogues," *Seminars in Dialysis*, 15(5):352-357 (2000).

Baird et al., "Steroid Dynamics Under Steady-State Conditions," *Recent Prog. Horm. Res.*, 25:611-664 (1969).

Barger-Lux M.J. et al., "Vitamin D and Its Major Metabolites: Serum Levels After Graded Oral Dosing in Healthy Men" *Osteoporosis International*, United Kingdom, 8(3):222-230 (1998).

Barreto et al., "25-Hydroxyvitamin $D_3$, the Prohormone of 1,25-Dihydroxyvitamin $D_3$, Inhibits the Proliferation of Primary Prostatic Epithelial Cells," *Cancer Epidemiol, Biomarkers & Prevention*, 9:265-270 (2000).

Beckman, et al., "Up-Regulation of the Intestinal 1, 25-Dihydroxyvitamin D Receptor During Hypervitaminosis D: A Comparison Between Vitamin D2 and Vitamin D31," *Biochemical and Biophysical Research Communications*, vol. 169, No. 3, pp. 910-915 (Jun. 29, 1990).

Beer et al., "Pharmacokinetics and Tolerability of a Single Dose of DN-101, a New Formulation of Calcitriol, in Patients with Cancer," *Clin. Cancer Res.*, 11:7794-7799 (2005).

Bell et al., "Evidence that 1,25-Dihydroxyvitamin D3 Inhibits the Hepatic Production of 25-Hydroxyvitamin D in Man," *J. Clin. Invest.*, 74:1540-1544 (1984).

Belostotsky et al., "A single high dose of ergocalciferol can be used to boost 25-hydroxyvitamin D levels in children with kidney disease," *Pediatr Nephrol*, 24:625-626 (2009).

Bianchi et al., "No Difference in Intestinal Strontium Absorption After an Oral or an Intravenous 1,25(OH)$_2$D$_3$ Bolus in Normal Subjects," *J. Bone Miner. Res.*, 14:1789-1795 (1999).

Blair et al., "Prevalence of vitamin D [25(OH)D] deficiency and effects of supplementation with ergocalciferol (vitamin D2) in stage 5 chronic kidney disease patients." *J.Ren Nutr.*, 18: 375-382 (2008).

Bordier et al., "Evolution of renal osteodystrophy: Correlation of bone histomorphometry and serum mineral and immunoreactive parathyroid hormone values before and after treatment with calcium carbonate or 25-hydroxycholecalciferol," *Kidney Int Suppl*, 2:S102-S112 (1975).

Bouillon et al., "Influence of dialysate calcium concentration and vitamin D on serum parathyroid hormone during repetitive dialysis," *Kidney Int.*, 7:422-432 (1975).

Brossard et al. "Influence of Glomerular Filtration Rate on Non-(1-84) Parathyroid Hormone (PTH) Detected by Intact PTH Assays," *Clinical Chemistry*, 46(5):697-703 (2000).

Buccianti et al., "Effects of Calcifediol Treatment on the Progression of Renal Osteodystrophy during Continuous Ambulatory Peritoneal Dialysis," *Nephron*, 56:353-356 (1990).

Budavari (ed.), Merck Index: an Encyclopedia of Chemicals, Drugs, and Biologicals, 11th Edition, Merck & Co., 9927-9930 (1989).

Bulla et al., "Renal bone disorders in children: therapy with vitamin D3 or 1,25-dihydroxycholecalciferol," *Proc.Eur.Dial.Transplant.Assoc.*, 16: 644-648 (1979).

Chandra et al., "Cholecalciferol (vitamin D3) therapy and vitamin D insufficiency in patients with chronic kidney disease: a randomized controlled pilot study," *Endocr.Pract.*, 14: 10-17 (2008).

Claris-Appiani et al., "Phosphate-Induced PTH Stimulation and Calcitriol Treatment in Children with Early Chronic Renal Insufficiency," *J. Bone Miner. Met.*, 12:S91-S97 (1994).

Coburn, "An Update on Vitamin D as Related to Nephrology Practice: 2003," *Kidney International*, vol. 64, Supplement 87, pp. S125-S130 (2003).

Coburn, et al., "Use of Active Vitamin D Sterols in Patients with Chronic Kidney Disease, Stages 3 and 5," *Kidney International*, vol. 63, Supplement 85, pp. S49-S53 (2003).

Coen et al., "1,25(OH)$_2$D$_3$ and 25-OHD$_3$ in the Treatment of Renal Osteodystrophy: Comparison of Combined Versus 1,25(OH)$_2$D$_3$ Administration Alone," *Miner. Electrolyte Metab.*, 9:19-27 (1983).

Coen et al., "25-hydroxycholecalciferol in the treatment of renal osteodystrophy in haemodialysed patients," *Int J Artificial Organs*, 2(6): 278-281 (1979).

Cohen-Solal et al., "Non-Aluminic Adynamic Bone Disease in Non-Dialyzed Uremic Patients: A New Type of Osteopathy Due to Overtreatment?" *Bone*, 13:1-5 (1992).

Collet et al. "Modified-Release Peroral Dosage Forms," Aulton (ed.), Pharmaceutics: The Science of Dosage Forms, Churchill Livingston, London, pp. 289-305 (2002).

Colodro et al., "Effect of 25-Hydroxy-Vitamin D3 on Intestinal Absorption of Calcium in Normal Man and Patients With Renal Failure," *Metabolism*, 27(6):745-753 (1978).

Cooke et al., "Vitamin D-Binding Protein (Gc-Globulin): Update 1995," *Endocrine Rev.*, 4:125-128 (1995).

Daisley-Kydd et al., "Calcitriol in the Management of Secondary Hyperparathyroidism of Renal Failure," *Pharmacotherapy.*, 16:619-630 (1996).

Davies, M. et al. The Absorption and Metabolism of Vitamin D3 from Parenteral Injection Sites, Proceedings of the Workshop on Vitamin D, 4th, Vitam. D: Basic Res. Its Clin. Appl. (1979), abstract.

DB-Pharma, "Dedrogyl 15 Mg/10ML Calcifediol Oral Drops, Solution," Marketing Authorization No. 317 863.2 (2000).

DeLuca, "Treatment of renal osteodystrophy with 25-hydroxycholecalciferol," *Arch Intern Med*, 126(5):896-899 (1970).

Deroisy et al., "Comparison of the Short-Term Effects of Three Oral Calcium-Vitamin D Formulations and Placebo on Calcium Metabolism," *Curr. Ther. Res.*, 59:370-378 (1998).

DeVille et al., "Effect of Ergocalciferol Supplementation on Serum Parathyroid Hormone and Serum 25-Hydroxyvitamin D in Chronic Kidney Disease," *Nephrology*, 11:555-559 (2006).

*Dietary Reference Intakes for Calcium, Phosphorus, Magnesium, Vitamin D, and Fluoride*, Standing Committee on the Scientific Evaluation of Dietary Reference Intakes, Food and Nutrition Board, Institute of Medicine, National Academy Press, Washington DC, pp. 250-287 (1997).

*Dietary Supplement Fact Sheet: Vitamin D*, National Institutes of Health, Office of Dietary Supplements (last update: Aug. 5, 2005), retrieved from URL:http:ods.od.nih.gov/factsheets/vitamind.asp on Aug. 31, 2007.

*Disease and Vitamin D*, University of California Riverside, retrieved from Internet, <URL: <http://vitamind.ucr.edu/disease.html>> (last update: May 19, 1999).

Disintegration, chapter 701; Dissolution, chapter 711; Distilling Range, chapter 721; Drug Release chapter 724; Electrophoresis, chapter 726; pp. 276-292, in: U.S. Pharmacopeia vol. 30, 2004.

Dogan et al., "Effect of depot oral cholecalciferol treatment on secondary hyperparathyroidism in stage 3 and stage 4 chronic kidney diseases patients," *Ren Fail.*, 30: 407-410 (2008).

Drueke et al., Recurrence of hyperparathyroidism from autografted parathyroid fragments in uremic patients in spite of administration of 25(OH)D3 and 1a(OH)D3. In: Vitamin D. Basic Research and its Clinical Application, (Eds. Norman AW, Schaefer K, Herrath Dv, Grigoleit HG, Coburn JW, DeLuca HF, Mawer EB, and Suda T), pp. 791-794. Willem de Gruyter, New York (1979).

Dusso et al, "Metabolic Clearance Rate and Production Rate of Calcitriol in Uremia," *Kidney Int.*, 35 860-864 (1989).

Dusso et al., "Extra-renal production of calcitriol in chronic renal failure," *Kidney Int.*, 34:368-375 (1988).

Dusso et al., "Extrarenal Production of Calcitrol in Normal and Uremic Humans*," *Journal of Clinical Endocrinology and Metabolism*, 72(1):157-164 (1991).

Eastwood et al., "Biochemical and histological effects of 1,25 dihydroxycholecalciferol (1,25-DHCC) in the osteomalacia of chronic renal failure," *J Urol Nephrol* (Paris,) 80(12): 984-985 (1974).

Eastwood et al., "The Effect of 25-Hydroxy Vitamin $D_3$ in the Osteomalacia of Chronic Renal Failure," *Clin. Sci. Molec. Med.*, 52:499-508 (1977).

Eastwood et al., "The contrasting effects on bone histology of vitamin D and of calcium carbonate in the osteomalacia of chronic renal failure," *Clin Sci Molec Med*, 47:23-42 (1974).

Fernandez et al., "Guidelines for Dosing of Intravenous Calcitriol in Dialysis Patients with Hyperparathyroidism," *Nephroi. Dial. Transplant.*, 11:96-101 (1996).

Fournier et al., "1-alpha-Hydroxycholecalciferol and 25-Hydroxycholecalciferol in Renal Bone Disease," *Calcified Tissues 1975: Proceedings of the 11th European Symposium on Calcified Tissues*, 226-235 (1975).

Fournier et al., "Advances in Nephrology from the Necker Hospital" *Adv. Nephrol Necker Hosp.* 21:237-306 (1992).

Fournier et al., "Comparison of 1α-hydroxycholecalciferol and 25-hydroxycholecalciferol in the treatment of renal osteodystrophy: Greater effect of 25-hydroxycholecalciferol on bone mineralization" Kidney International 15:196-204 (1979).

Fournier et al., "Current Status of the Management of Renal Osteodystrophy" *Proceedings of the European Dialysis and Transplant Association* 15:547-568 (1978).

Fournier et al., "Importance of Vitamin D Repletion in Uraemia," *Nephrol Dial Transplant*, 14(4):819-823 (1999).

Fournier et al., "Low doses of calcitriol or calcium carbonate for the prevention of hyperparathyroidism in predialysis patients?" *Nephrol Dial Transplant* 11(7):1493-1495 (1996).

Fournier et al., "Present-Day Concepts in the Treatment of Chronic Renal Failure" *Contrib Nephrol*. 71:64-80 (1989).

Fournier et al., "Preventing Renal Bone Disease in Moderate Renal Failure with $CaCO_3$ and 25(OH) Vitamin $D_3$," *Kidney Int.*, 33:S178-S279 (1988).

Fournier et al., "Renal Osteodystrophy in Dialysis Patients: Diagnosis and Treatment," *Artificial Organs*, 22:530-557 (1998).

Fournier et al., "Renal Osteodystrophy: Pathophysiology and Treatment" *Hormone Res.* 20:44-58 (1984).

Fournier et al., "The Approach to the Treatment of Secondary Hyperparathyroidism in Early Renal Failure" *Am. J. Nephrol* 8:170-172 (1988).

Fournier et al., "Traitement vitaminique D et ostéodystrophies rénales: indications et modalitiés" Nephrologie 16(2):165-190 (1995) [journal in French].

Fournier et al., 1α Hydroxycholecalciferol and 25 Hydroxycholecalciferol in Renal Bone Disease Proc Eur Dial Transplant Assoc 12:227-236 (1976).

Fournier, "Vitamin D: Biochemical, Chemical, and Clinical Aspects Related to Calcium Metabolism," Vitamin D: Proceedings of the Third Workshop on Vitamin D, Asilomar, Pacific Grove, CA, USA 667-669 (1977).

Friedman et al. "The Role of Vitamin D in Mild to Moderate Chronic Kidney Disease," *Trends in Endocrinology & Metab,*. 13(5):189-194 (2002).

Frohling et al., "Serum 25-hydroxyvitamin D in patients with chronic renal failure on long-term treatment with high doses of vitamin D2." *Nephron* 26: 116-120 (1980).

Frost et al., "Histomorphometric Changes in Trabecular Bone of Renal Failure Patients Treated with Calcifediol," *Metab. Bone Dis. & Rel. Res.*, 2:285-295 (1981).

Gallagher et al., "Comparison of the Histological Effect and Metabolism of 25-(OH)D and 1,25-(OH)2D in Rat Bone," p. 399-401, IN: Norman, *Vitamin D: Basic Research and its Clinical Application: Proceedings of the Fourth Workshop on Vitamin D*, Berlin, West Germany, Feb. 1979.

Ghazali et al., "Is low plasma 25-(OH) vitamin D a major risk factor for hyperparathyroidism and Looser's zones independent of calcitriol?" *Kidney International* 55:2169-2177 (1999).

Haddad et al., "Acute Administration of 25-Hydroxycholecalciferol in Man," *J. Clin. Endocrinol. Metab*., 42:284-289 (1976).

Haddad et al., "Human Serum Binding Capacity and Affinity for 25-Hydroxyergocalciferol and 25-Hydroxycholecalciferol," *J. Clin. Endocrinol. Metab.*, 43:86-91 (1976).

Haddad et al., "Natural and Synthetic Sources of Circulating 25-Hydroxyvitamin D in Man," *Nature*, 244:515-517 (1973).

Haddad, "Plasma Vitamin D-binding Protein (Gc-Globulin): Multiple Tasks," *J. Steroid Biochem. Molec. Biol.*, 53:579-582 (1995).

Haddad, "Seasonal Diminution of Vitamin D Stores in the United States: Can Darker Winters Lead to Lighter Bones?" *Trends Endocrinol. Metab.*, 7:209-212 (1996).

Haddad, "Traffic, Binding and Cellular Access of Vitamin D Sterols," *Bone and Mineral Res.*, Elsevier, 5:281-308 (1987).

Haddad, "Vitamin D—Solar Rays, The Milky Way, or Both?" *NEJM*, 326:1213-1215 (1992).

Haldimann et al., "Effect of an Oral Dose of 25-Hydroxyvitamin D3 on Its Blood Levels in Patients with the Nephrotic Syndrome," *J Clin Endocrinology and Metabolism*, 50(3): 470-474 (1980).

Halloran et al., "Plasma Vitamin D Metabolite Concentrations in Chronic Renal Failure: Effect of Oral Administration of 25-Hydroxyvitamin D3," *J. Clin. Endocrin. & Metab.*, 59:1063-1069 (1984).

Hamida et al., Hyperparathyroïdie secondaire ál"insuffisance rénale" Annales d'Endocrinologie 55:147-158 (1994) [reference in French].

Hannula et al., "Constant, But Not Pulsed Calcitriol Suppresses Hemodialysis Patients' Antigen-Induced Lymphocyte Proliferation," *Nephron*, 86:139-144 (2000).

Hari et al., "Vitamin D insufficiency and effect of cholecalciferol in children with chronic kidney disease," *Pediatr.Nephrol,*. 25: 2483-2488 (2010).

Hay et al., "Vitamin D2 in Vertebrate Evolution," *Comp. Biochem. Physiol. B*, 56:375-380 (1977).

Hodson et al., "Treatment of childhood renal osteodystrophy with calcitriol or ergocalciferol," *Clin Nephrology*, 24(4): 192-200 (1985).

Holick, "Vitamin D Deficiency in CKD: Why Should We Care?" *Am. J. Kidney Dis.*, 45:1119-1121 (2005).

Hollis, "Circulating 25-Hydroxyvitamin D Levels Indicative of Vitamin D Sufficiency: Implications for Establishing a New Effective Dietary Intake Recommendation for Vitamin D," *J. Nutr.* 135: 317-322 (2005).

Horst et al., "A Sensitive Competitive Protein Binding Assay for Vitamin D in Plasma," *Steroids*, 37:581-592 (1981).

Horst et al., "Discrimination in the Metabolism of Orally Dosed Ergocalciferol and Cholecalciferol by the Pig, Rat and Chick," *Biochem. J.*, 204:185-189 (1982).

Horst et al., "Rat cytochrome P450C24 (CYP24) does not metabolize 1,25-dihydroxyvitamin $D_2$ to calcitroic acid," *J. Cell Biochem.*, 88:282-285 (2003).

Hottelart et al., "Ostéodystrophie rénale (2): son traitement chez l'insuffisant rénal avant la dialyse" Nephrologie 21(6):275-282 (2000) [reference in French].

Houghton et al., "The Case Against Ergocalciferol (Vitamin $D_2$) as a Vitamin Supplement," *Am. J. Clin. Nutr.*, 84:694-697 (2006).

Hunt, et al., "A Comparison of the Toxicity of Ergocalciferol and Cholecalciferol in Rhesus Monkeys (*Macaca mulatta*)," J. Nutrition, 102:975-986 (1972).

Hussar, "New Drugs of 1999," *J. Am. Pharmacist. Assoc.* 40(2):181-229 (2000).

International Search Report of counterpart PCT/US2008/061579 dated Aug. 21, 2008 (5 pages).

International Search Report of PCT/US2007/061521 dated Jul. 17, 2007 (6 pages).

Ishimura et al., "Serum Levels of 1,25-Dihydroxyvitamin D, 24,25-Dihydroxyvitamin D, and 25-Hydroxyvitamin D in Nondialyzed Patients with Chronic Renal Failure," *Kidney Int.*, 55:1019-1027 (1999).

Jara et al., "Effect of Calcitriol Treatment and Withdrawal on Hyperparathyroidism in Haemodialysis Patients with Hypocalcaemia," *Nephrol. Dial. Transplant.*, 16:1009-1016 (2001).

Jean et al., "Daily Oral 25-Hydroxycholecalciferol Supplementation for Vitamin D Deficiency in Haemodialysis Patients: Effects on Mineral Metabolism and Bone Markers," *Nephrol. Dial. Transplant*, 23:3670-3676 (2008).

Jean et al., "Evidence for Persistent Vitamin D 1-Alpha-Hydroxylation in Hemodialysis Patients: Evolution of Serum 1,25-Dihydroxycholecalciferol after 6 Months of 25-Hydroxycholecalciferol Treatment" *Nephron. Clin. Pract.* 110:c58-c65 (2008).

Jean et al., "Monthly cholecalciferol administration in heamodialysis patients: a simple and efficient strategy for vitamin D supplementation" *Nephrol. Dial. Transplant* 24(12):3799-3805 (2009).

Jones., "Expanding the Role for Vitamin D in Chronic Kidney Disease: Importance of Blood 25-OH-D Levels and Extra-Renal 1α-Hydroxyase in the Classical and Nonclassical Actions of 1α, 25-Dihydroxyvitamin $D_3$," *Seminars in Dialysis*, 20(4):316-324 (2007).

Jones, "Pharmacokinetics of vitamin D toxicity," *Am. J. Clin. Nutr.* 88(suppl): 582S-6S (2008).

Kajihara et al., "Novel Method to Control Release of Lipophilic Drugs with High Potency from Silicone," *Chem. Pharm. Bull.*, 51:11-14 (2003).

Kalantar-Zadeh et al., "Clinical Outcomes with Active versus Nutritional Vitamin D Compounds in Chronic Kidney Disease" *Clin J Am Soc Nephrol.* 4(9):1529-1539 (2009).

Kanis et al., "Rate of Reversal of Hypercalcaemia and Hypercalciuria Induced by Vitamin D and Its 1-alpha-Hydroxylated Derivatives," *BMJ*, 1:78-81 (1977).

Kim, *Advanced Pharmaceutics: Physicochemical Principles*, pp. 362-392, Boca Raton, Fla: CRC Press (2004).

Kleinman et al., "Effects of Calcifediol on Calcified Tissue in Uremia," *Arch Intern Med*, 138: 864-865 (1978).

Kooienga et al., "The effect of combined calcium and vitamin D3 supplementation on serum intact parathyroid hormone in moderate CKD," *Am.J.Kidney Dis,.* 53: 408-416 (2009).

Koshikawa, et al., "Clinical Effect of Intravenous Calcitriol Administration on Secondary Hyperparathyroidism," Nephron; 90:413-423 (2002).

LaClair et al., "Prevalence of Calcidiol Deficiency in CKD: A Cross-Sectional Study Across Latitudes in the United States," *Am. J. Kidney Dis.*, 45:1026-1033 (2005).

Lafage et al., "Ketodiet, Physiological Calcium Intake and Native Vitamin D Improve Renal Osteodystrophy," *Kidney Int.*, 42:1217-1225 (1992).

Lambert et al., "Evidence for Extrarenal Production of 1-alpha,25-Dihydroxyvitamin D in Man," *J. Clin. Invest.*, 69:722-725 (1982).

Lambrey et al., "24, 25 Dihydroxycalciferol: Assay in Non-Anephric Patients on Chronic Haemodialysis and Assessment of it's Possible Pathophysiological Role in Renal Osteodystrophy" *Proc Eur Dial Transplant Assoc.* 17:548-556 (1980).

Lambrey, "Possible Link Between Changes in Plasma 24,25-Dihydroxyvitamin D and Healing of Bone Resorption in Dialysis Osteodrstophy" *Metab. Bone Dis. & Rel. Res.* 4:25-30 (1982).

Langman et al., "25-Hydroxyvitamin D3 (Calcifediol) Therapy of Juvenile Renal Osteodystrophy: Beneficial Effect on Linear Growth Velocity," *J. Pediatrics*, 100:815-820 (1982).

Larrosa M. et al., Long-Term Treatment of Hypovitaminosis D. Calcidol or Cholecalciferol? *Annals of the Rheumatic Diseases*, vol. 64, No. Suppl. 3, Jul. 2005, p. 366.

Lau et al., "Vitamin D Therapy of Osteoporosis: Plain Vitamin D Therapy Versus Active Vitamin D Analog (D-Hormone) Therapy," *Calcif. Tissue Int.*, 65:295-306 (1999).

Lehmann et al., "Coating of Tablets and Small Particles with Acrylic Resins by Fluid Bed Technology," *Int. J. Pharm. Tech. & Prod. Mfr.*, 2:31-43 (1981).

Letteri et al., "Effects of 25-Hydroxycholecalciferol on Calcium Metabolism in Chronic Renal Failure" Adv. Exp. Med. Biol. 81:591-601 (1977).

Lips et al., "A Global Study of Vitamin D Status and Parathyroid Function in Postmenopausal Women with Osteoporosis: Baseline Data from the Multiple Outcomes of Raloxifene Evaluation Clinical Trial," *The Jour. of Clin. Endo. & Meta.*, 86(3):1212-1221 (2001).

Lomonte et al., "Are Low Plasma Levels of 25-(OH) Vitamin D a Major Risk Factor for Hyperparathyroidism Independent of Calcitriol in Renal Transplant Patients?" *J. Nephrol.*, 18:96-101 (2005).

Lund et al., "Serum 1,25-Dihydroxycholecalciferol in Anephric. Haemodialyzed and Kidney-transplanted Patients," *Nephron*, 25:30-33 (1980).

Maierhofer et al., "Synthesis and Metabolic Clearance of 1,25-Dihydroxyvitamin D as Determinants of Serum Concentrations: a Comparison of Two Methods" Journal of Clinical Endocrinology and Metabolism 53:472-475 (1981).

Manni et al., "Oral Calcitriol: Comparison Between the Same Weekly Dose Administered as a Single vs. Two Divided Pulsed Doses in Secondary Hyperparathyroidism of Chronic Renal Failure," *Ital. J Mineral Electrolyte Metab.*, 11:61-64 (1997).

Matsushita et al., "Clinical effects of 25-hydroxycholecalciferol in patients with chronic renal failure," *J Nutr Sci Vitaminol*, 23:257-261 (1977).

Mazouz et al., "Risk factors of renal failure progression two years prior to dialysisis" Clinical Nephroloby 51 (6):355-366 (1999).

Mazur, "Effects of 25-OHD3 on Renal Function in Pediatric Patients with Chronic Renal Failure," *Mineral Electrolyte Metab.* 10:351-358 (1984).

Memmos et al., "Response of uremic osteoid to vitamin D," *Kidney Int*, 21(Suppl. 11): S50-S54 (1982).

Menon et al., "Vitamin D insufficiency and hyperparathyroidism in children with chronic kidney disease," Pedaitr Nephrol, 23:1831-1836 (2008).

Messa et al., "Direct in Vivo Assessment of Parathyroid Hormone-Calcium Relationship Curve in Renal Patients," *Kidney Int.*, 46:1713-1720 (1994).

Moe et al., "A randomized trial of cholecalciferol versus doxercalciferol for lowering parathyroid hormone in chronic kidney disease," *Clin.J.Am.Soc.Nephrol.* 5: 299-306 (2010).

Moe et al., "Safety and Efficacy of Pulse and Daily Calcitriol in Patients on CAPD: A Randomized Trial," *Nephrol. Dial. Transplant.*, 13:1234-1241 (1998).

Morris, "Vitamin D: A Hormone for All Seasons—How Much is Enough?" *Clin. Biochem. Rev.*, 26:21-32 (2005).

Muindi et al., "Phamacokinetics of Liquid Calcitriol Formulation in Advanced Solid Tumor Patients: Comparison with Caplet Formulation," *Cancer Chemother. Pharmacol.*, 56:492-496 (2005).

Naik et al., "Effects of Vitamin D Metabolites and Analogues on Renal Function," *Nephron*, 28:17-25 (1981).

Nakanishi et al., "The Roles of Vitamin D in Secondary Hyperparathyroidism," [journal in Japanese] 52:1107-1112 (2004).

Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).

Oksa et al., "Effects of long-term cholecalciferol supplementation on mineral metabolism and calciotropic hormones in chronic kidney disease," *Kidney Blood Press Res.*, 31: 322-329 (2008).

Parfitt et al., "Calcitriol But No Other Metabolite of Vitamin D is Essential for NormalBone Growth and Development in the Rat," *J. Clin. Invest.*, 73:576-586 (1984).

Peacock et al., "Effect of Calcium or 25OH Vitamin D3 Dietary Supplementation on Bone Loss at the Hip in Men and Women over the Age of 60" *The Journal of Clinical Endocrinology & Metabolism*, 85(9):3011-3019 (2007).

Phadnis et al., "Direct, Rapid Effects of 25-Hydroxyvitamin D3 on Isolated Intestinal Cells," *J. Cell. Biochem.*, 90:287-293 (2003).

Pourgholami et al., "1, 25-Dihydroxyvitamin $D_3$ Dissolved in Lipiodol Produces a Sustained Antiproliferative Effect in the Human Hepatoblastoma Cell Line HepG2," *Anticancer Res.*, 20:723-728 (2000).

Pourgholami et al., "In Vitro Antiproliferative Activity of a Medium-Chain Triglyceride Solution of 1, 25-Dihydroxyvitamin $D_3$ in HepG2 Cells," *Anticancer Res.*, 20:4257-4260 (2000).

Rapuri, P.B. et al., "Effect of Vitamins D2 and D3 Supplement Use on Serum 25-OHD Concentration in Elderly Women in Summer and Winter," Calcified Tissue International, 74(2):150-156 (2004).

Recker et al., "The Efficacy of Calcifediol in Renal Osteodystrophy," *Arch. Intern. Med.*, 138:857-863 (1978).

Reddy et al., Abstracts Sixth Annual Scientific Meeting of the American Society for Bone and Mineral Research, 36:524 (1984).

Reichel et al., "Calcium Metabolism in Early Chronic Renal Failure: Implications for the Pathogenesis of Hyperparathyroidism," *Nephrol. Dial. Transplant.*, 6:162-169 (1991).

Reichel et al., "Intermittent Versus Continuous Administration of 1,25-dihydroxyvitamin $D_3$ in experimental renal hyperparathyroidism," *Kidney Int.*, 44:1259-1265 (1993).

Reichel, "Current treatment options in secondary renal hyperparathyroidism," *Nephrol Dial Transplant* 21:23-28 (2006).

Ritter et al., "25-Hydroxyvitamin $D_3$ suppresses PTH synthesis and secretion by bovine parathyroid cells," *Kidney Int.*, 70:654-659 (2006).

Rucker et al., "Vitamin D insufficiency and treatment with oral vitamin D3 in northern-dwelling patients with chronic kidney disease," *J.Nephrol.* 22: 75-82 (2009).

Russell et al., "Therapeutic Effects of 25-Hydroxyvitamin D3 on Renal Osteodystrophy," *Mineral Electrolyte Metab.*, 1:129-138 (1978).

Rutherford et al., "Effect of 25-Hydroxycholecalciferol on Calcium Absorption in Chronic Renal Disease," Kidney International, 8:320-324 (1975).

Saab et al., "Prevalence of Vitamin D Deficiency and the Safety and Effectiveness of Monthly Ergocalciferol in Hemodialysis Patients," *Nephron Clin. Pract.*, 105:c132-c138 (2007).

Sanchez, "Prevention and Treatment of Renal Osteodystrophy in Children With Chronic Renal Insufficiency and End-Stage Renal Disease," *Seminars in Nephrology*, 21:441-450 (2001).

Sebert et al. "Comparative effects of equal doses of vitamin D2 and vitamin D3 for the correction of vitamin D deficiency in the elderly" in Norman et al. (eds.), Vitamin D—Gene Regulation, Structure-Function Analysis and Clinical Application: Proceedings of the Eighth Workshop on Vitamin d Paris, France, pp. 765-766, New York: Walter De Gruyter Inc. (1991).

Sebert et al., "Effets a Long Terme D'Une Association De 25-Hydroxycholécalciférol et de 1-Alpha-Hydroxycholécalciférol Sur L'Ostéodystrophie Des Hémodialysés Chroniques" Rev. Rhum Mal Osteoartic 48(7-9):535-541 (1981).

Sebert et al., "Limit by Hyperphosphatemia of the Usefulness of Vitamin D Metabolites (1 alpha-Hydroxycholecalciferol and 25-Hydroxycholecalciferol) in the Treatment of Renal Osteodystrophy," *Metab. Bone Dis. & Rel. Res.*, 2:217-222 (1980).

Sekkarie, "The Impact of Over-the-counter Vitamin D Supplementals on Vitamin D and Parathyroid Hormone Levels in Chronic Kidney Disease," *Clin. Nephrology*, 65:91-96 (2006).

Shah et al., "Prevalence and correction of 25(OH) vitamin D deficiency in peritoneal dialysis patients," *Peritoneal Dialysis Int.*, 25:362-366 (2005).

Sjoden, et al., "1α-Hydroxyvitamin $D_2$ is Less Toxic than 1α-Hydroxyvitamin $D_3$ in the Rat," Society for Experimental Biology and Medicine, 179: 432-436 (1985).

Somerville et al., "Resistance to Parathyroid Hormone in Renal Failure: Role of Vitamin D Metabolites," *Kidney Int.*, 14:245-254 (1978).

Sommerfeldt et al., "Metabolism of Orally Administered [$^3$H]Ergocalciferol and [$^3$H]Cholecalciferol by Dairy Calves," *J. Nutr.*, 113:2595-2600 (1983).

Soob et al., "Prevalence of Vitamin D Deficiency and the Safety and Effectiveness of Monthly Ergocalciferol in Hemodialysis Patients," *Nephron Clin. Pract.*, 105:c132-c138 (2007).

Stamp et al., "Comparison of Oral 25-Hydroxycholecalciferol, Vitamin D, and Ultraviolet Light as Determinants of Circulating 25-Hydroxyvitamin D," *The Lancet*, 1341-1343 (Jun. 25, 1977).

Stein et al., "An Update on the Therapeutic Potential of Vitamin D Analogues," *Expert Opin. Investig. Drugs*, 12:825-840 (2003).

Stubbs et al., "Cholecalciferol supplementation alters calcitriol-responsive monocyte proteins and decreases inflammatory cytokines in ESRD," *J.Am.Soc.Nephrol.*, 21: 353-361 (2010).

Stumpf, "The Dose Makes the Medicine," *Drug Discovery Today*, 11:550-555 (2006).

Szycher, *Szycher's Dictionary of Biomaterials and Medical Devices*, pp. 20, 48, 127, Lancaster, Penn: Technomic Publishing Co., Inc. (1992).

Sömjen et al., "Nonhypercalcemic Analogs of Vitamin D Stimulate Creatine Kinase B Activity in Osteoblast-Like ROS 17/2.8 Cells and Up-Regulate Their Responsiveness to Estrogens," *Steroids*, 63:340-343 (1998).

Taylor et al., "Interrelationship of Serum 25-Hydroxyvitamin $D_3$ and 1,25-Dihydroxyvitamin D in Juvenile Renal Osteodystrophy after Therapy with 25-Hydroxyvitamin $D_3$," *Metab. Bone Dis. & Rel. Res.*, 4:255-261 (1982).

Taylor et al., "The absence of 24,25-dihydroxycholecalciferol in anephric patients," *Clin.Sci.Mol.Med.Suppl.*, 55: 541-547 (1978).

Taylor, CM, 24,25-Dihydroxyvitamin D in Human Serum. In: Vitamin D. Basic Research and Clinical Applications, pp. 197-203. Walter de Gruyter, New York (1979).

Teitelbaum et al., "Calcifediol in Chronic Renal Insufficiency" *JAMA* 235(2):164-167 (1976).

Teitelbaum et al., "Tetracycline fluorescence in uremic and primary hyperparathyroid bone," *Kidney Int.*, 12:366-372 (1977).

Thomas et al., "Hypovitaminosis D in Medical Inpatients," *NEJM*, 338:777-783 (1998).

Thombre, "Assessment of the feasibility of oral controlled release in an exploratory development setting," *Drug Discovery Today*, 10(17): 1159-1166 (2005).

Tokmak et al., "High-dose cholecalciferol to correct vitamin D deficiency in haemodialysis patients," *Nephrol.Dial.Transplant.*, 23: 4016-4020 (2008).

Trakarnvanich et al., "Effect of high dose ergocalciferol in chronic kidney disease patients with 25-hydroxyvitamin D deficiency," *J.Med.Assoc.Thai.* 93: 885-891 (2010).

Van Weelden et al., "Apoptotic Regression of MCF-7 Xenografts in Nude Mice Treated with the Vitamin $D_3$ Analog, EB1089," *Endocrinology*, 139:2102-2110 (1998).

Verberckmoes et al., "Osteodystrophy of Dialysed Patients Treated with Vitamin D," *Proc Eur Dial Transplant Assoc.*, 10(0): 217-226 (1973).

Vieth, "What is the optimal vitamin D status for health?" *Prog. Biophys. Mol. Biol.*, 92:26-32 (2006).

Wise (ed.), *Handbook of Pharmaceutical Controlled Release Technology*, "An Overview of Controlled Release Systems," Chapter 22, pp. 431-445, 461-463; Research and Development Aspects of Oral Controlled-Release Dosage Forms, Chapter 23, pp. 465-473, New York: Marcel Dekker, Inc. 3 (2000).

Witmer et al., "Effects of 25-hydroxycholecalciferol on bone lesions of children with terminal renal failure" *Kidney International* 10:395-408 (1976).

Written Opinion of counterpart PCT/US2007/061521 dated Jul. 17, 2007 (8 pages).

Written Opinion of counterpart PCT/US2008/061579 dated Aug. 21, 2008 (6 pages).

Zerwekh et al., "Extra-Renal Production of 24,25-Dihydroxyvitamin D in Chronic Renal Failure During 25 Hydroxyvitamin $D_3$ Therapy," *Kidney Int.*, 23:401-406 (1983).

Zisman et al., "Impact of Ergocalciferol Treatment of Vitamin D Deficiency on Serum Parathyroid Hormone Concentrations in Chronic Kidney Disease," *Am. J. Nephrol.*, 27:36-43 (2007).

Zucchelli et al., "Therapeutic effects of 25-hydroxycholecalciferol and sodium etidronate on renal osteodystrophy," *Mineral.Electrolyte Metab.* 7: 86-96 (1982).

Skelly et al., In vitro and in vivo testing and correlation for oral controlled/modified-release dosage forms. *Pharm. Res.*, 7(9):975-82 (1990).

Gibson, ed., Product optimisation. *Pharmaceutical Preformulation and Formulation: A Practical Guide from Candidate Drug Selection to Commercial Dosage Form*, 295-98 (2004).

\* cited by examiner

METHOD FOR TREATING SECONDARY HYPERPARATHYROIDISM IN CKD

CROSS-REFERENCE TO RELATED APPLICATIONS

This application is a continuation of U.S. patent application Ser. No. 12/109,983 filed Apr. 25, 2008, which claims the benefit of priority under 35 U.S.C. §119(e) of U.S. Provisional Patent Application Ser. No. 60/913,853 filed Apr. 25, 2007. The disclosure of each priority application is incorporated herein by reference.

BACKGROUND

1. Field of the Disclosure

The disclosure relates generally to controlled release pharmaceutical compositions. More particularly, the invention relates to a controlled-release formulation for oral delivery of a Vitamin D compound.

2. Brief Description of Related Technology

Cholecalciferol and ergocalciferol (collectively are referred to as "Vitamin D") are fat-soluble seco-steroid precursors to Vitamin D prohormones. The Vitamin D metabolites known as 25-hydroxyvitamin $D_2$ and 25-hydroxyvitamin $D_3$ (collectively referred to herein as "25-hydroxyvitamin D") are fat-soluble steroid prohormones to Vitamin D hormones that contribute to the maintenance of normal levels of calcium and phosphorus in the bloodstream.

Cholecalciferol and ergocalciferol are normally present at stable, low concentrations in human blood. Slight, if any increases in blood Vitamin D levels occur after meals since unsupplemented diets have low Vitamin D content, even those containing foods fortified with Vitamin D. Almost all human Vitamin D supply comes from fortified foods, exposure to sunlight or from dietary supplements, with the latter source becoming increasingly important. Blood Vitamin D levels rise only gradually, if at all, after sunlight exposure since cutaneous 7-dehydroxycholesterol is modified by UV radiation to pre-Vitamin $D_3$, which undergoes thermal conversion in the skin to cholecalciferol over a period of several days before circulating in the blood. In contrast, supplements such as those currently available, do cause marked increases in intraluminal, blood and intracellular levels of Vitamin D proportional to the dose administered.

Both cholecalciferol and ergocalciferol are metabolized into prohormones by enzymes primarily located in the liver of the human body. Cholecalciferol is metabolized into a prohormone 25-hydroxyvitamin $D_3$, and ergocalciferol is metabolized into two prohormones, 25-hydroxyvitamin $D_2$ and 24(S)-hydroxyvitamin $D_2$. Cholecalciferol and ergocalciferol also can be metabolized into prohormones outside of the liver in certain cells, such as enterocytes, by enzymes which are identical or similar to those found in the liver. Elevating concentrations of either precursor increases prohormone production; similarly, lowering precursor concentrations decreases hormone production. Surges in the blood levels of cholecalciferol and/or ergocalciferol ("cholecalciferol/ergocalciferol") can transiently raise intracellular Vitamin D concentrations, accelerating prohormone production and elevating intracellular and blood prohormone concentrations. Surges in the blood levels of cholecalciferol and/or ergocalciferol also can saturate the enzymes which produce the prohormones, causing the excess Vitamin D to be catabolized or shunted to long-term storage in adipose tissue. Vitamin D stored in adipose tissue is less available for future conversion to prohormones. Surges in intraluminal levels of Vitamin D after ingestion of current oral supplements can directly boost Vitamin D and prohormone concentrations in the local enterocytes, thereby exerting "first pass" effects on calcium and phosphorus metabolism in the small intestine.

The Vitamin D prohormones are further metabolized in the kidneys into potent hormones. The prohormone 25-hydroxyvitamin $D_3$ is metabolized into a hormone 1α,25-dihydroxyvitamin $D_3$ (or calcitriol); likewise, 25-hydroxyvitamin $D_2$ and 24(S)-hydroxyvitamin $D_2$ are metabolized into hormones known as 1α,25-dihydroxyvitamin $D_2$ and 1α,24(S)-dihydroxyvitamin $D_2$, respectively. Production of these hormones from the prohormones also can occur outside of the kidney in cells which contain the required enzyme(s).

Surges in blood or intracellular prohormone concentrations can promote excessive extrarenal hormone production, leading to local adverse effects on calcium and phosphorus metabolism. Such surges also can inhibit hepatic prohormone production from subsequent supplemental Vitamin D and promote catabolism of both Vitamin D and 25-hydroxyvitamin D in the kidney and other tissues.

Blood Vitamin D hormone concentrations remain generally constant through the day in healthy individuals, but can vary significantly over longer periods of time in response to seasonal changes in sunlight exposure or sustained changes in Vitamin D intake. Normally, blood levels of cholecalciferol, ergocalciferol and the three Vitamin D prohormones are also constant through the day, given a sustained, adequate supply of Vitamin D from sunlight exposure and an unsupplemented diet. Blood levels of cholecalciferol and ergocalciferol, however, can increase markedly after administration of currently available Vitamin D supplements, especially at doses which greatly exceed the amounts needed to prevent Vitamin D deficiency, rickets or osteomalacia.

The Vitamin D hormones have essential roles in human health which are mediated by intracellular Vitamin D receptors (VDR). In particular, the Vitamin D hormones regulate blood calcium levels by controlling the absorption of dietary calcium by the small intestine and the reabsorption of calcium by the kidneys. Excessive hormone levels can lead to abnormally elevated urine calcium (hypercalciuria), blood calcium (hypercalcemia) and blood phosphorus (hyperphosphatemia). The Vitamin D hormones also participate in the regulation of cellular differentiation and growth, parathyroid hormone (PTH) secretion by the parathyroid glands, and normal bone formation and metabolism. Further, Vitamin D hormones are required for the normal functioning of the musculoskeletal, immune and renin-angiotensin systems. Numerous other roles for Vitamin D hormones are being postulated and elucidated based on the documented presence of intracellular VDR in nearly every human tissue.

Secondary hyperparathyroidism is a disorder which develops primarily because of Vitamin D deficiency. It is characterized by abnormally elevated blood levels of PTH and, in the absence of early detection and treatment, it becomes associated with parathyroid gland hyperplasia and a constellation of metabolic bone diseases. It is a common complication of chronic kidney disease (CKD), with rising incidence as CKD progresses. Secondary hyperparathyroidism can also develop in individuals with healthy kidneys, due to environmental, cultural or dietary factors which prevent adequate Vitamin D supply.

As to secondary hyperparathyroidism and its occurrence in CKD, there is a progressive loss of cells of the proximal nephrons, the primary site for the synthesis of the vitamin D hormones (collectively "1,25-dihydroxyvitamin D") from 25-hydroxyvitamin $D_3$ and 25-hydroxyvitamin $D_2$. In addition, the loss of functioning nephrons leads to retention of excess phosphorus which reduces the activity of the renal 25-hydroxyvitamin D-1α-hydroxylase, the enzyme which catalyzes the reaction to produce the D hormones. These two events account for the low serum levels of 1,25-dihydroxyvitamin D commonly found in patients with moderate to severe CKD when Vitamin D supply is adequate.

Reduced serum levels of 1,25-dihydroxyvitamin D cause increased, and ultimately excessive, secretion of PTH by direct and indirect mechanisms. The resulting hyperparathyroidism leads to markedly increased bone turnover and its sequela of renal osteodystrophy, which may include a variety of other diseases, such as, osteitis fibrosa cystica, osteomalacia, osteoporosis, extraskeletal calcification and related disorders, e.g., bone pain, periarticular inflammation and Mockerberg's sclerosis. Reduced serum levels of 1,25-dihydroxyvitamin D also can cause muscle weakness and growth retardation with skeletal deformities (most often seen in pediatric patients).

Blood levels of 1,25-dihydroxyvitamin D are precisely regulated by a feedback mechanism which involves PTH. The renal 1α-hydroxylase (or CYP27B1) is stimulated by PTH and inhibited by 1,25-dihydroxyvitamin D. When blood levels of 1,25-dihydroxyvitamin D fall, the parathyroid glands sense this change via intracellular Vitamin D receptors and secrete PTH. The secreted PTH stimulates expression of renal CYP27B1 and, thereby, increases production of Vitamin D hormones. As blood concentrations of 1,25-dihydroxyvitamin D rise again, the parathyroid glands attenuate further PTH secretion. As blood PTH levels fall, renal production of Vitamin D hormones decreases. Rising blood levels of 1,25-dihydroxyvitamin D also directly inhibit further Vitamin D hormone production by CYP27B1.

PTH secretion can be abnormally suppressed in situations where blood 1,25-dihydroxyvitamin D concentrations become excessively elevated, as can occur in certain disorders such as sarcoidosis or as a result of bolus doses of Vitamin D hormone replacement therapies. Oversuppression of PTH secretion can cause or exacerbate disturbances in calcium homeostasis. The parathyroid glands and the renal CYP27B1 are exquisitely sensitive to changes in blood concentrations of Vitamin D hormones such that serum 1,25-dihydroxyvitamin D is tightly controlled, fluctuating up or down by less than 20% during any 24-hour period. In contrast to renal production of Vitamin D hormones, extrarenal production is not under precise feedback control.

Blood levels of 1,25-dihydroxyvitamin D and substrate 25-hydroxyvitamin D prohormone, and regulation thereof, can also be affected by vitamin D hormone analogs, such as 1α-hydroxyvitamin $D_2$ and 19-nor-1,25 dihydroxyvitamin $D_2$.

The actions of Vitamin D hormones on specific tissues depend on the degree to which they bind to (or occupy) the intracellular VDR in those tissues. Cholecalciferol and ergocalciferol have affinities for the VDR which are estimated to be at least 100-fold lower than those of the Vitamin D hormones. As a consequence, physiological concentrations of cholecalciferol and ergocalciferol exert little, if any, biological actions without prior metabolism to Vitamin D hormones. However, supraphysiologic levels of cholecalciferol and ergocalciferol, in the range of 10 to 1,000 fold higher than normal, can sufficiently occupy the VDR and exert actions like the Vitamin D hormones. Similarly, the prohormones 25-hydroxyvitamin $D_2$ and 25-hydroxyvitamin $D_3$ have essentially identical affinities for the VDR which are also estimated to be at least 100-fold lower than those of the Vitamin D hormones. As a consequence, physiological concentrations of 25-hydroxyvitamin $D_2$ and 25-hydroxyvitamin $D_3$ have little, if any, biological actions without prior metabolism to Vitamin D hormones. However, supraphysiologic levels of 25-hydroxyvitamin $D_2$ and 25-hydroxyvitamin $D_3$, in the range of 10 to 1,000 fold higher than normal, can sufficiently occupy the VDR to exert actions like the Vitamin D hormones.

Production of Vitamin D prohormones declines when Vitamin D is in short supply, as in conditions such as Vitamin D insufficiency or Vitamin D deficiency (alternatively, hypovitaminosis D). Low production of Vitamin D prohormones leads to low blood levels of 25-hydroxyvitamin D. Inadequate Vitamin D supply often develops in individuals who are infrequently exposed to sunlight, have chronically inadequate intakes of Vitamin D, or suffer from conditions that reduce the intestinal absorption of fat soluble vitamins (such as Vitamin D). It has recently been reported that most individuals living in northern latitudes have inadequate Vitamin D supplies. Left untreated, inadequate Vitamin D supply can cause serious bone disorders, including rickets and osteomalacia.

The Institute of Medicine (TOM) of the National Academy of Sciences has concluded that an Adequate Intake (AI) of Vitamin D for a healthy individual ranges from 200 to 600 IU per day, depending on the individual's age and sex. See Standing Committee on the Scientific Evaluation of Dietary Reference Intakes, Dietary reference intakes: calcium, phosphorus, magnesium, vitamin D, and fluoride, Washington, D.C.: National Academy Press (1997), incorporated herein by reference. The AI for Vitamin D was defined primarily on the basis of serum 25-hydroxyvitamin D level sufficient to prevent Vitamin D deficiency, rickets or osteomalacia (or at least 11 ng/mL). The TOM also established a Tolerable Upper Intake Level (UL) for Vitamin D of 2,000 IU per day, based on evidence that higher doses are associated with an increased risk of hypercalciuria, hypercalcemia and related sequelae, including cardiac arrhythmias, seizures, and generalized vascular and other soft-tissue calcification.

Currently available oral Vitamin D supplements are far from ideal for achieving and maintaining optimal blood 25-hydroxyvitamin D levels. These preparations typically contain 400 IU to 5,000 IU of Vitamin $D_3$ or 50,000 IU of Vitamin $D_2$ and are formulated for quick or immediate release in the gastrointestinal tract. When administered at chronically high doses, as is often required for Vitamin D repletion, these products have significant and, often, severe limitations which are summarized below.

High doses of immediate release Vitamin D supplements produce marked surges in blood Vitamin D levels, thereby promoting: (a) storage of Vitamin D in adipose tissue, which is undesirable because stored Vitamin D is less available for later hepatic conversion to 25-hydroxyvitamin D; (b) hepatic catabolism of Vitamin D to metabolites, which are less useful or no longer useful for boosting blood 25-hydroxyvitamin D levels, via 24- and/or 26-hydroxylation; and, (c) excessive intracellular 24- or 25-hydroxylation of Vitamin D, which leads to increased risk of hypercalciuria, hypercalcemia and hyperphosphatemia.

High doses of immediate release Vitamin D supplements also produce surges or spikes in blood and intracellular 25-hydroxyvitamin D levels, thereby promoting: (a) excessive extrarenal production of Vitamin D hormones, and leading to local aberrations in calcium and phosphorus homeostasis and increased risk of hypercalciuria, hypercalcemia and hyperphosphatemia; (b) accelerated catabolism of both Vitamin D and 25-hydroxyvitamin D by 24- and/or 26-hydroxylation in the kidney and other tissues; (c) down-regulation of hepatic production of Vitamin D prohormones, unnecessarily impeding the efficient repletion of Vitamin D insufficiency or deficiency; and, (d) local aberrations in calcium and phosphorus homeostasis mediated by direct binding to VDR.

Furthermore, high doses of immediate release Vitamin D supplements produce supraphysiologic pharmacological concentrations of Vitamin D, e.g., in the lumen of the duodenum, promoting: (a) 25-hydroxylation in the enterocytes and local stimulation of intestinal absorption of calcium and phosphorus, leading to increased risk of hypercalciuria, hypercalcemia and hyperphosphatemia; (b) catabolism of Vitamin D by 24- and/or 26-hydroxylation in the local enterocytes, causing decreased systemic bioavailability; and (c) absorption primarily via chylomicrons, leading to increased hepatic catabolism.

Vitamin D supplementation above the UL is frequently needed in certain individuals; however, currently available oral Vitamin D supplements are not well suited for maintaining blood 25-hydroxyvitamin D levels at optimal levels given the problems of administering high doses of immediate release Vitamin D compounds.

Blood Vitamin D hormone concentrations also remain generally constant through the day in healthy individuals, but can vary significantly over longer periods of time in response to seasonal changes in sunlight exposure or sustained alterations in Vitamin D intake. Marked differences in normal Vitamin D hormone levels are commonly observed among healthy individuals, with some individuals having stable concentrations as low as approximately 20 pg/mL and others as high as approximately 70 pg/mL. Due to this wide normal range, medical professionals have difficulty interpreting isolated laboratory determinations of serum total 1,25-dihydroxyvitamin D; a value of 25 pg/mL may represent a normal value for one individual or a relative deficiency in another.

Transiently low blood levels of 1,25-dihydroxyvitamin D stimulate the parathyroid glands to secrete PTH for brief periods ending when normal blood Vitamin D hormone levels are restored. In contrast, chronically low blood levels of 1,25-dihydroxyvitamin D continuously stimulate the parathyroid glands to secrete PTH, resulting in a disorder known as secondary hyperparathyroidism. Chronically low hormone levels also decrease intestinal calcium absorption, leading to reduced blood calcium concentrations (hypocalcemia) which further stimulate PTH secretion. Continuously stimulated parathyroid glands become increasingly hyperplastic and eventually develop resistance to regulation by vitamin D hormones. Without early detection and treatment, secondary hyperparathyroidism progressively increases in severity, causing debilitating metabolic bone diseases, including osteoporosis and renal osteodystrophy.

Chronically low blood levels of 1,25-dihydroxyvitamin D develop when there is insufficient renal CYP27B1 to produce the required supply of Vitamin D hormones, a situation which commonly arises in CKD. The activity of renal CYP27B1 declines as the Glomerular Filtration Rate (GFR) falls below approximately 60 ml/min/1.73 m² due to the loss of functioning nephrons. In end-stage renal disease (ESRD), when the kidneys fail completely and hemodialysis is required for survival, renal CYP27B1 often becomes altogether absent. Any remaining CYP27B1 is greatly inhibited by elevated serum phosphorous (hyperphosphatemia) caused by inadequate renal excretion of dietary phosphorous.

Chronically low blood levels of 1,25-dihydroxyvitamin D also develop because of a deficiency of Vitamin D prohormones, since renal hormone production cannot proceed without the required precursors. Prohormone production declines markedly when cholecalciferol and ergocalciferol are in short supply, a condition often described by terms such as "Vitamin D insufficiency," "Vitamin D deficiency," or "hypovitaminosis D." Therefore, measurement of 25-hydroxyvitamin D levels in blood has become the accepted method among healthcare professionals to monitor Vitamin D status. Recent studies have documented that the great majority of CKD patients have low blood levels of 25-hydroxyvitamin D, and that the prevalence of Vitamin D insufficiency and deficiency increases as CKD progresses.

It follows that individuals most vulnerable to developing chronically low blood levels of 1,25-dihydroxyvitamin D are those with CKD. Most CKD patients typically have decreased levels of renal CYP27B1 and a shortage of 25-hydroxyvitamin D prohormones. Not surprisingly, most CKD patients develop secondary hyperparathyroidism. Unfortunately, early detection and treatment of secondary hyperparathyroidism in CKD is rare, let alone prevention.

The National Kidney Foundation (NKF) has recently focused the medical community's attention on the need for early detection and treatment of secondary hyperparathyroidism by publishing Kidney Disease Outcomes Quality Initiative (K/DOQI) Clinical Practice Guidelines for Bone Metabolism and Disease in Chronic Kidney Disease [Am. J. Kidney Dis. 42:S1-S202, 2003)]. The K/DOQI Guidelines identified the primary etiology of secondary hyperparathyroidism as chronically low blood levels of 1,25-dihydroxyvitamin D and recommended regular screening in CKD Stages 3 through 5 for elevated blood PTH levels relative to stage-specific PTH target ranges, which for Stage 3 is 35-70 pg/mL (equivalent to 3.85-7.7 pmol/L), for Stage 4 is 70-110 pg/mL (equivalent to 7.7-12.1 pmol/L), and for Stage 5 is 150-300 pg/mL (equivalent to 16.5-33.0 pmol/L) (defined in K/DOQI Guideline No. 1). In the event that screening revealed an iPTH value to be above the ranges targeted for CKD Stages 3 and 4, the Guidelines recommended a follow-up evaluation of serum total 25-hydroxyvitamin D to detect possible Vitamin D insufficiency or deficiency. If 25-hydroxyvitamin D below 30 ng/mL was observed, the recommended intervention was Vitamin D repletion therapy using orally administered ergocalciferol. If 25-hydroxyvitamin D above 30 ng/mL was observed, the recommended intervention was Vitamin D hormone replacement therapy using known oral or intravenous Vitamin D hormones or analogs. The Guidelines did not recommend the concurrent application of Vitamin D repletion and Vitamin D hormone replacement therapies, consistent with warnings mandated by the Food and Drug Administration in package inserts for Vitamin D hormone replacement products.

The NKF K/DOQI Guidelines defined Vitamin D sufficiency as serum 25-hydroxyvitamin D levels ≧30 ng/mL. Recommended Vitamin D repletion therapy for patients with "Vitamin D insufficiency," defined as serum 25-hydroxyvitamin D of 16-30 ng/mL, was 50,000 IU per month of oral Vitamin $D_2$ for 6 months, given either in single monthly doses or in divided doses of approximately 1,600 IU per day. Recommended repletion therapy for patients with "Vitamin D deficiency" was more aggressive: for "mild" deficiency, defined as serum 25-hydroxyvitamin D of 5-15 ng/mL, the Guidelines recommended 50,000 IU per week of oral Vitamin $D_2$ for 4 weeks, followed by 50,000 IU per month for another 5 months; for "severe" deficiency, defined as serum 25-hydroxyvitamin D below 5 ng/mL, the Guidelines recommended 50,000 IU/week of oral Vitamin $D_2$ for 12 weeks, followed by 50,000 IU/month for another 3 months. Doses of 50,000 IU per week are approximately equivalent to 7,000 IU per day.

SUMMARY

One aspect of the disclosure provides a solid or semi-solid, waxy pharmaceutical formulation for controlled release of a vitamin D compound in the gastrointestinal tract of a subject which ingests the formulation. The formulation includes a waxy controlled release carrier agent, a lipoidic agent, an oily vehicle for the vitamin D compound, and a vitamin D compound. The formulation provides for controlled release of the vitamin D compound incorporated therein. The formulation preferably is free of or essentially free of disintegrants.

In another aspect, the invention provides a controlled-release dosage form of a vitamin D compound that contains (a) a pharmacologically active amount of a vitamin D compound and (b) a release-modifying agent that controls the release rate of the vitamin D compound from the dosage form to reduce Cmax and/or delay Tmax and/or decrease $Cmax_{24hr}/C_{24hr}$ as described herein. Preferably both Cmax is reduced and Tmax is delayed (increased). Such controlled-release dosage forms exhibit the advantage of increased elimination half-life and/or reduced toxicity and/or improved potency (e.g., ability to administer a reduced dosage of vitamin D compound, or administer less often, to achieve a similar therapeutic effect compared to an immediate release dosage form). In some embodiments, the release-modifying agent includes a waxy controlled release carrier agent, a lipoidic agent, and an oily vehicle for the vitamin D compound. Optionally, the release-modifying agent and dosage forms of the invention may be free or substantially free of disintegrants.

Thus, one embodiment of the invention is a method of administering an amount of a vitamin D compound to a patient such that the maximum serum concentration of the vitamin D compound in a dose interval (Cmax) is reduced as compared to Cmax for an equivalent amount of a vitamin D compound administered by bolus IV injection and/or an equivalent immediate-release, oral dosage form. Similarly, the invention provides a controlled-release dosage form having a quantity of a vitamin D compound that, when administered to a patient, results in a Cmax less than Cmax for an equivalent amount of a vitamin D compound administered by bolus IV injection and/or by an equivalent immediate-release, oral dosage form. For example, the reduction is preferably by a factor of at least 20%, 30%, 40%, 50%, 60%, 70%, or 80%.

Another embodiment of the invention is a method of administering an amount of a vitamin D compound to a patient such that the maximum change in serum concentration of a vitamin D compound in a dose interval is reduced as compared to an equivalent amount of a vitamin D compound administered by bolus IV injection and/or an equivalent immediate-release, oral dosage form. Similarly, the invention provides a controlled-release dosage form having a quantity of a vitamin D compound that, when administered to a patient, results in a maximum change in serum concentration of a vitamin D compound in a dose interval less than an equivalent amount of a vitamin D compound administered by bolus IV injection and/or by an equivalent immediate-release, oral dosage form. For example, the reduction is preferably by a factor of at least 20%, 30%, 40%, 50%, 60%, 70%, or 80%.

Still another embodiment of the invention is a method of administering an amount of a vitamin D compound to a patient such that the ratio of the maximum serum concentration within 24 hours after administration of a vitamin D compound to the concentration 24 hours after administration ($Cmax_{24hr}/C_{24hr}$) is reduced as compared to an equivalent amount of a vitamin D compound administered by bolus IV injection and/or an equivalent immediate-release, oral dosage form. Similarly, the invention provides a controlled-release dosage form having a quantity of a vitamin D compound that, when administered to a patient, results in $Cmax_{24hr}/C_{24hr}$ less than an equivalent amount of a vitamin D compound administered by bolus IV injection and/or by an equivalent immediate-release, oral dosage form. For example, the reduction is preferably by a factor of at least 20%, 30%, 40%, 50%, 60%, 70%, or 80%.

Yet another embodiment of the invention is a method of administering an amount of a vitamin D compound to a patient such that the elimination half-life ($t_{1/2}$) of a vitamin D compound is increased as compared to $t_{1/2}$ for an equivalent amount of a vitamin D compound administered by bolus IV injection and/or an equivalent immediate-release, oral dosage form. Similarly, the invention provides a controlled-release dosage form having a quantity of a vitamin D compound that, when administered to a patient, results in a $t_{1/2}$ of a vitamin D compound greater than that of $t_{1/2}$ for an equivalent amount of a vitamin D compound administered by bolus IV injection and/or by an equivalent immediate-release, oral dosage form. For example, the increase is preferably by a factor of at least 25%, 30%, 40%, 50%, 60%, 70%, 80%, 90%, 100%, 200%, or 300%.

A further embodiment of the invention is a method of administering an amount of a vitamin D compound to a patient such that the time for the plasma concentration of a vitamin D compound to reach its maximum in a dose interval following administration (Tmax) is increased as compared to Tmax for an equivalent amount of a vitamin D compound administered by bolus IV injection and/or an equivalent immediate-release, oral dosage form. Similarly, the invention provides a controlled-release dosage form having a quantity of a vitamin D compound that, when administered to a patient, results in Tmax greater than that of an equivalent amount of a vitamin D compound administered by bolus IV injection and/or by an equivalent immediate-release, oral dosage form. For example, the increase is preferably by a factor of at least 25%, 30%, 40%, 50%, 60%, 70%, 80%, 90%, 100%, 200%, 300%, 500%, or 1000%.

In various embodiments, the compositions are contemplated to be associated with one or more benefits, such as significantly: increasing the bioavailability of the contained vitamin D compound by promoting absorption directly into the bloodstream rather than into the lymphatic system via chylomicrons; increasing the bioavailability of the contained vitamin D compound by reducing catabolism in the enterocytes of the upper small intestine; decreasing the undesirable first pass effects of the contained vitamin D compound on the duodenum; avoiding production of adverse supraphysiologic surges in blood levels of the vitamin D compound; preventing reduction of blood concentrations of the vitamin D compound below optimal levels; restoring blood concentrations of the vitamin D compound to optimal levels; maintaining blood concentrations of the vitamin D compound at such optimal levels; decreasing disruptions in Vitamin D metabolism and related aberrations in PTH, calcium and phosphorus homeostasis; and decreasing the risk of serious side effects associated with vitamin D repletion and replacement, including hypercalciuria, hypercalcemia, hyperphosphatemia, and vitamin D toxicity. One or more of the aforementioned benefits may be seen independently or in combination.

For the compositions and methods described herein, preferred steps, preferred components, preferred compositional ranges thereof, and preferred combinations of the foregoing, can be selected from the various examples provided herein.

Further aspects and advantages will be apparent to those of ordinary skill in the art from a review of the following detailed description, taken in conjunction with the drawings. While the compositions and methods are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

For further facilitating the understanding of the present invention, twenty-seven drawing figures are appended hereto.

FIG. 7 shows an overlay of comparative data for immediate and controlled release formulations.

DETAILED DESCRIPTION

Figure 1:
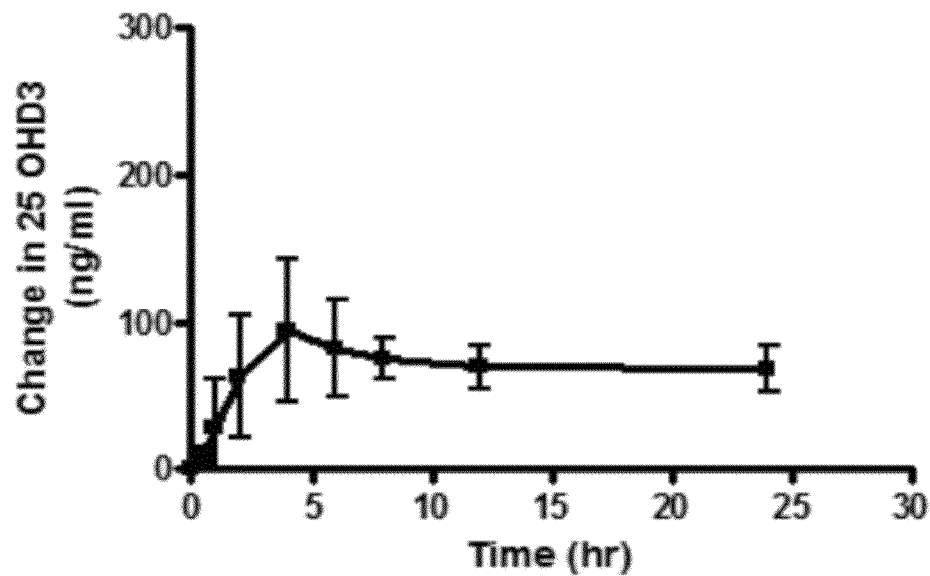
FIG. 1 through FIG. 8 show plots of the change in serum 25-hydroxyvitamin $D_3$ levels over the first 24 hours post-administration for groups of test subjects administered oral dosage formulations including 25-hydroxyvitamin $D_3$ according to Example 1. In addition.
Figure 2:
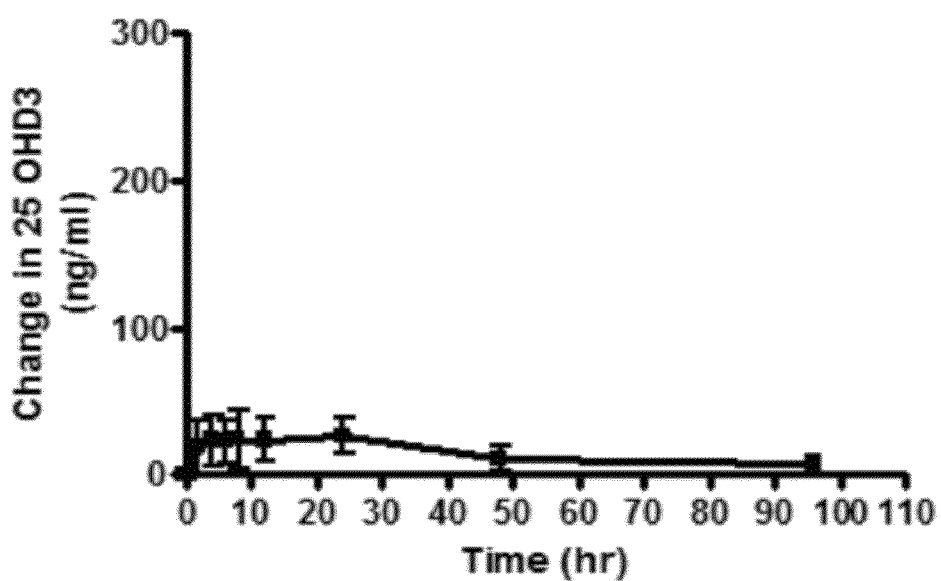
Figure 3:
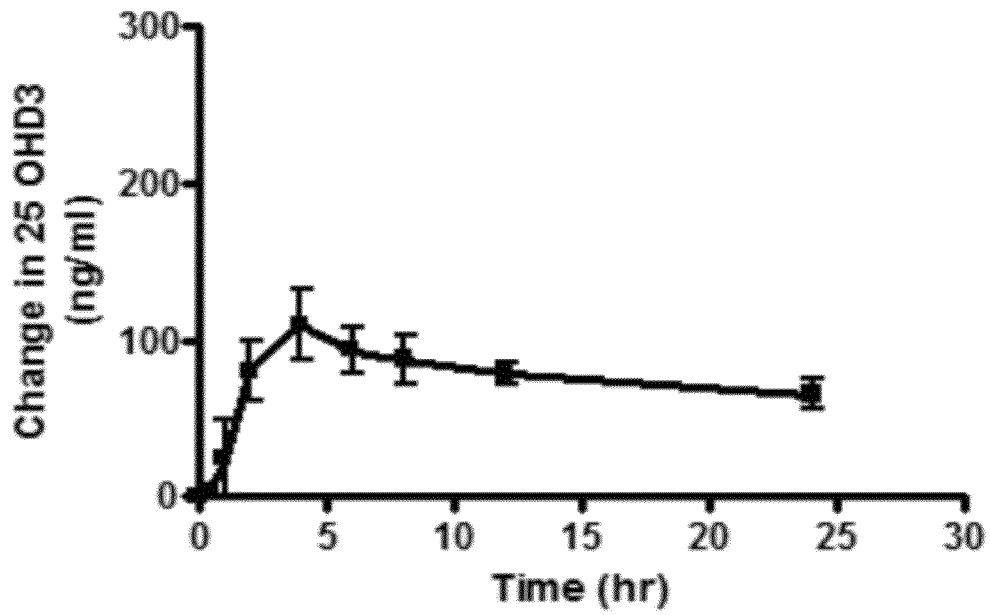
Figure 4:
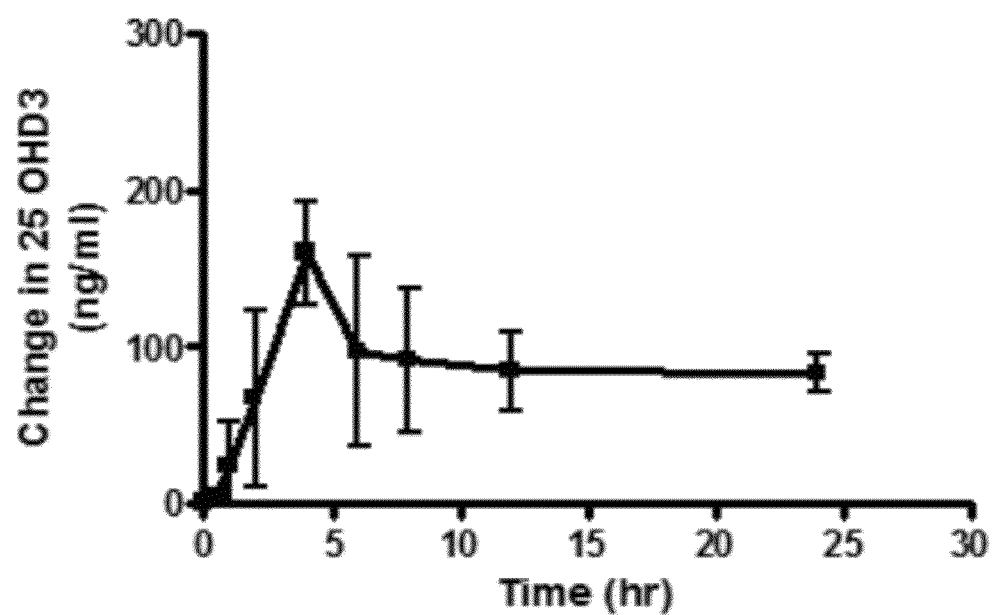
Figure 5:
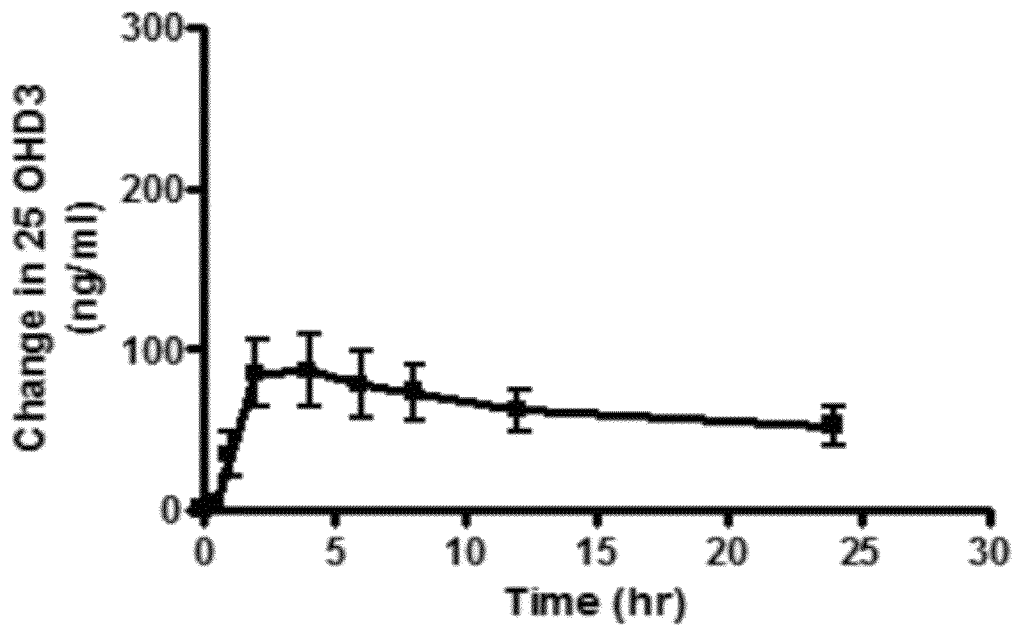
Figure 6:
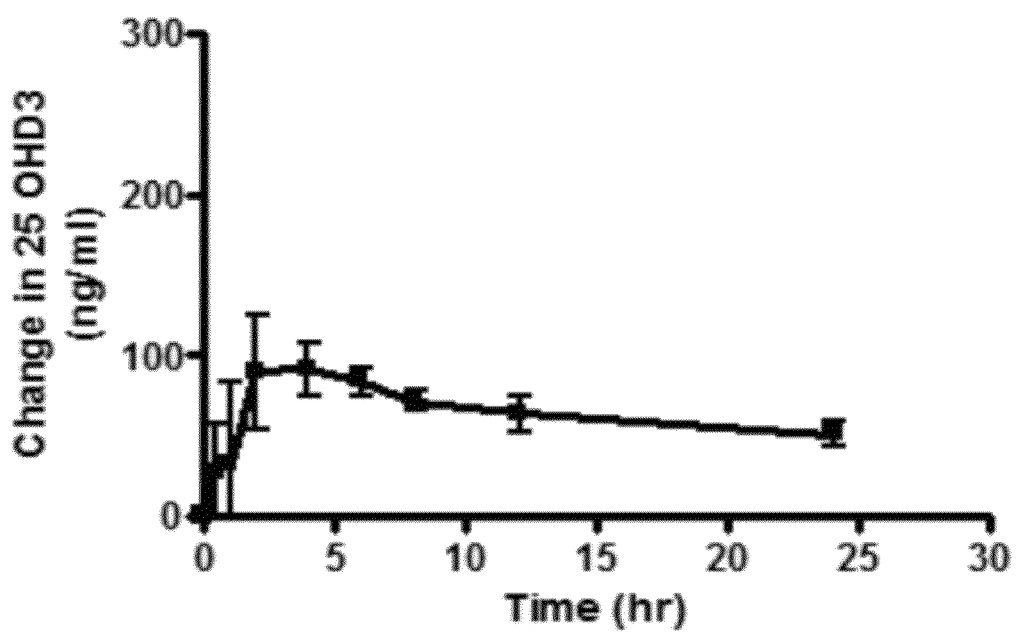
Figure 7:
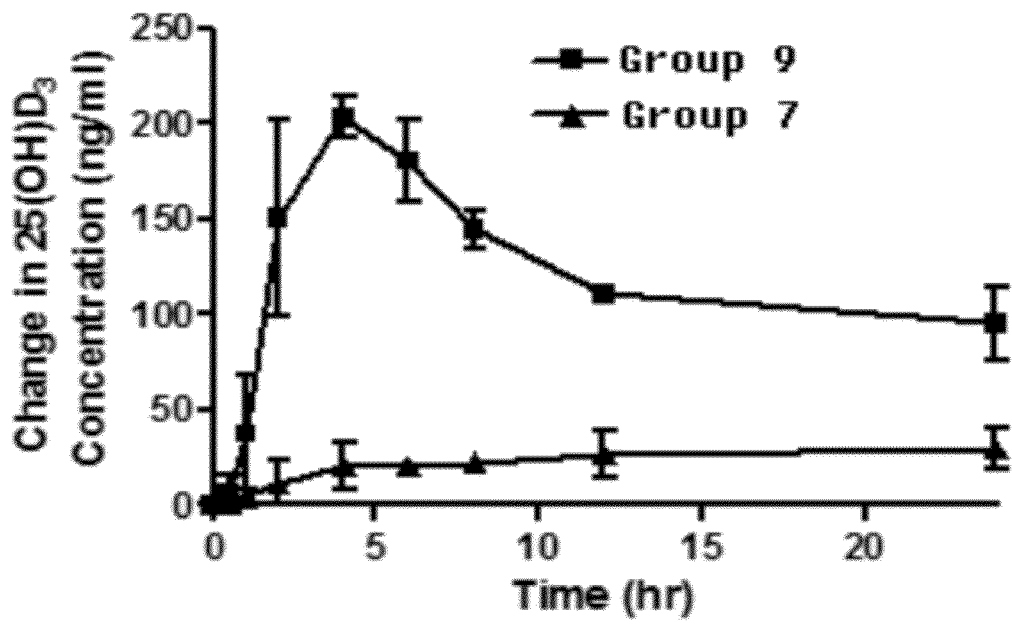
Figure 8:
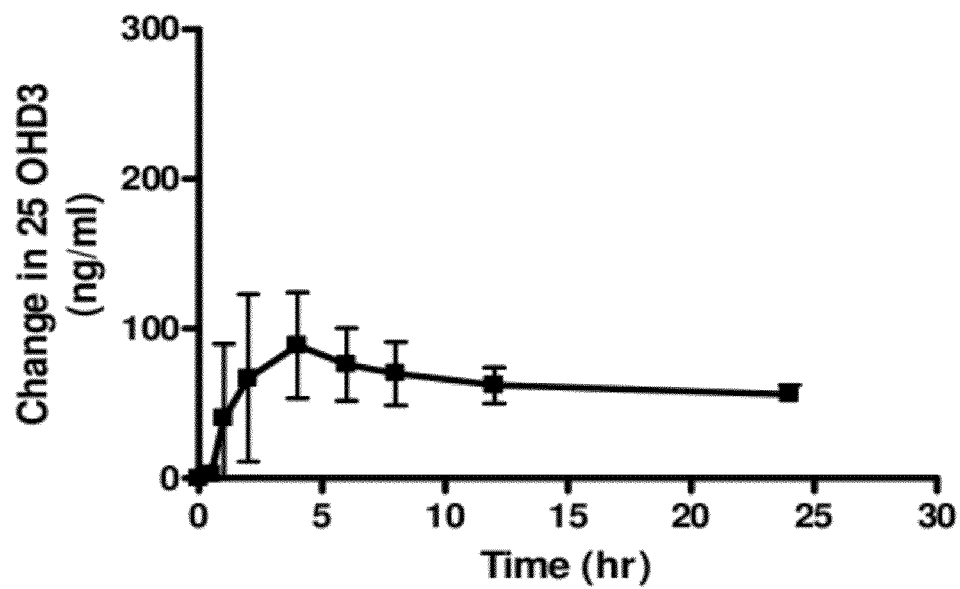

As used herein, the term "Vitamin D toxicity" is meant to refer to the side effects suffered from excessively elevated Vitamin D blood levels, including one or more of nausea, vomiting, polyuria, hypercalciuria, hypercalcemia and hyperphosphatemia.

"Vitamin D insufficiency and deficiency" is generally defined as having serum 25-hydroxyvitamin D levels below 30 ng/mL (see National Kidney Foundation guidelines, NKF, Am. J. Kidney Dis. 42:S1-S202 (2003), incorporated herein by reference).

As used herein the term "hypercalcemia" refers to condition in a patient wherein the patient has corrected serum levels of calcium above 10.2 mg/dL. Normal corrected serum levels of calcium for a human are between about 8.6 to 10.2 mg/dL.

As used herein the term "hyperphosphatemia" refers to a condition in a patient having normal kidney function, or Stage 3-4 CKD, wherein the patient has serum phosphorous levels above 4.6 mg/dL. In a patient who has Stage 5 CKD, hyperphosphatemia occurs when the patient has serum levels above 5.5 mg/dL. Normal values for serum phosphorous in a human are 2.5-4.5 mg/dL.

As used herein the term "over suppression of plasma iPTH" refers to a condition in a patient having normal kidney function, or Stage 1-3 CKD, wherein the patient has levels of plasma iPTH below 15 pg/mL. In a patient having Stage 4 CKD, over suppression of plasma iPTH occurs when the patient has levels of plasma iPTH below 30 pg/mL. In a patient having Stage 5 CKD, over suppression of plasma iPTH occurs when the patient has levels of plasma iPTH below 100 pg/mL.

As used herein, the term "Vitamin D hormone replacement therapy" refers to the administration to a patient of an effective amount of an active vitamin D hormone such as 1,25-dihydroxyvitamin $D_3$ and/or 1,25-dihydroxyvitamin $D_2$, optionally together with or other metabolites and analogs of Vitamin D which can substantially occupy the intracellular VDR.

As used herein, the term "substantially constant" with respect to the serum or blood level of Vitamin D means that the release profile of the controlled release (defined hereinbelow) formulation should not include increases in total serum or blood levels of cholecalciferol and ergocalciferol of greater than approximately 10 nmol/L after administration of a unit dose, optionally over a period of at least 4 hours, 12 hours, 1 day, 2 days, 3 days, 4 days, or 5 days. The term "substantially constant" with respect to the serum or blood level of 25-hydroxyvitamin D prohormones means that the release profile of any formulation administered as detailed hereinbelow should not include transient increases in total serum or blood levels of 25-hydroxyvitamin D of greater than approximately 3 ng/mL after administration of a unit dose. The term "substantially constant" with respect to the serum or blood level of an active vitamin D hormone preferably means that the release profile of the controlled release formulation should not include increases in total serum or blood levels of 1,25-dihydroxyvitamin D of greater than approximately 75 pg/mL each after administration of a unit dose, optionally over a period of preferably at least 30 minutes or 4 hours, etc.

As used herein, the terms "controlled release," "sustained release," and "modified release" are used interchangeably, and refer to the release of the administered vitamin D compound in a way that deviates from immediate release. The terms "controlled release" and "modified release" optionally include delayed release characteristics. For example, a delayed release type of controlled release formulation will be characterized by Cmax at a time greater than Cmax for an immediate release formulation. As another example, the release of an administered vitamin D (cholecalciferol and/or ergocalciferol) and/or a 25-hydroxyvitamin D compound will preferably be at such a rate that total serum or blood levels of 25-hydroxyvitamin D are maintained or elevated above predosing levels for an extended period of time, e.g. 4 to 24 hours or even longer. As another example, a sustained release type of controlled release formulation will be characterized by release at such a rate that total serum or blood levels of a 1,25-dihydroxyvitamin D compound are maintained or elevated above predosing levels for an extended period of time, e.g. 20 to 40 minutes, 1 to 15 hours or even longer.

"Supraphysiologic" in reference to intraluminal, intracellular and blood levels of Vitamin D refers to a total concentration of the vitamin D compound markedly greater than the generally stable levels observed in a Vitamin D-replete subject, animal or human patient over the course of any 24-hour period by laboratory measurement when Vitamin D supplementation has been withheld for at least 30 days. "Adverse supraphysiologic surge" refers to a local or serum concentration of a vitamin D compound that elicits adverse effects such as excessive extrarenal hormone production, leading to local adverse effects on calcium and phosphorus metabolism, inhibition of hepatic 25-hydroxylation of vitamin D, increased catabolism of both Vitamin D and 25-hydroxyvitamin D, hypercalciuria, hypercalcemia and/or hyperphosphatemia, with possible cardiovascular sequelae.

As used herein, the term "hyperparathyroidism" refers to primary hyperparathyroidism, secondary hyperparathyroidism and hyperparathyroidism secondary to chronic kidney disease (Stage 3, 4 or 5).

The term "subject" as used herein generally includes humans, mammals (e.g., dogs, cats, rodents, sheep, horses, cows, goats), veterinary animals and zoo animals.

It also is specifically understood that any numerical value recited herein includes all values from the lower value to the upper value, i.e., all possible combinations of numerical values between the lowest value and the highest value enumerated are to be considered to be expressly stated in this application. For example, if a concentration range or a beneficial effect range is stated as 1% to 50%, it is intended that values such as 2% to 40%, 10% to 30%, or 1% to 3%, etc., are expressly enumerated in this specification. These are only examples of what is specifically intended.

Administration of 25-hydroxyvitamin $D_3$ in an immediate release oral formulation has been tried as an alternative method of Vitamin D supplementation. This approach, which was subsequently abandoned, caused problems as do the currently used Vitamin D supplements. Specifically, it produced surges or spikes in blood and intracellular 25-hydroxyvitamin D levels. Without intending to be bound by any particular theory, it is believed that surges or spikes in blood and intracellular 25-hydroxyvitamin D levels promote (a) competitive displacement of Vitamin D hormones from the serum Vitamin D Binding Protein (DBP) and excessive delivery of the displaced hormones to tissues containing VDR, and (b) transiently excessive renal and extrarenal production of Vitamin D hormones, which together led to local aberrations in calcium and phosphorus metabolism. In addition, these surges in blood 25-hydroxyvitamin D levels are believed to promote catabolism of both Vitamin D and 25-hydroxyvitamin D by 24- and/or 26-hydroxylation in the kidney and other tissues, down-regulation of hepatic production of Vitamin D prohormones, unnecessarily impeding the efficient repletion of Vitamin D insufficiency or deficiency, and, additional local aberrations in calcium and phosphorus homeostasis mediated by direct binding to VDR. Importantly, immediate release of 25-hydroxyvitamin $D_3$ is believed to promote its intestinal absorption via a mechanism substantially involving transport to the liver in chylomicrons, rather than bound to the serum DBP. Delivery of 25-hydroxyvitamin D to the liver via chylomicrons is believed to significantly increase the likelihood of its catabolism.

One aspect of the disclosure provides a solid or semi-solid, waxy pharmaceutical formulation for controlled release of a vitamin D compound in the gastrointestinal tract of a subject which ingests the formulation. The formulation includes a waxy controlled release carrier agent, a lipoidic agent, an oily vehicle for the vitamin D compound, and a vitamin D compound. The formulation provides for controlled release of the vitamin D compound incorporated therein. The formulation is free of or essentially free of disintegrants.

The waxy controlled release carrier provides for a formulation which is solid or semi-solid at room temperature and solid, semi-solid, or liquid at body temperature, preferably semi-solid or liquid at body temperature. Examples of carriers suitable for use include waxes, such as synthetic wax, microcrystalline wax, paraffin wax, carnauba wax, and beeswax; polyethoxylated castor oil derivatives, hydrogenated vegetable oils, glyceryl mono-, di- or tribehenates; long-chain alcohols, such as stearyl alcohol, cetyl alcohol, and polyethylene glycol; and mixtures of any of the foregoing. Non-digestible waxy substances, such as hard paraffin wax, are preferred.

The waxy carrier preferably is present in an amount greater than about 5% of the formulation, based on the total weight of the formulation excluding any additional coatings or shells (wt %). For example, the waxy carrier can comprise greater than 5 wt % of the formulation, greater than 10 wt % of the formulation, greater than 15 wt % of the formulation, greater than 20 wt % of the formulation, and greater than 25 wt % of the formulation. The waxy carrier is preferably present in an amount less than 50 wt %, less than 40 wt %, less than 35 wt %, or less than 30 wt. %. Suitable ranges include 5 wt % to 35 wt %, 15 wt % to 35 wt % and 20 to 30 wt %. Examples include 15 wt %, 16 wt %, 17 wt %, 18 wt %, 19 wt %, 20 wt %, 21 wt %, 22 wt %, 23 wt %, 24 wt %, 25 wt %, 26 wt %, 27 wt %, 28 wt %, 29 wt %, and 30 wt %.

The lipoidic agent provides for release of the vitamin D compound from the formulation in the gastrointestinal tract of the subject being treated. Without intending to be bound by any particular theory of operation, it is believed that the lipoidic agent can serve one or more preferred functions such as creating a micro-emulsion of the oily vehicle in gastrointestinal fluid; providing prolonged gastric retention, for example by bioadhesive properties such that the formulation interacts with the mucous layer of the stomach and/or intestine; and in enhancing absorption of the vitamin D compound. However, regardless of the mechanism of action, the invention is not limited by any particular mode of operation.

The lipoidic agent components preferably are amphiphiles, in which the molecule or ion contains both hydrophilic and lipophilic portions. These components can be defined by a numerical value based on the Hydrophile/Lipophile Balance system ("HLB system"). The HLB scale is a numerical scale, extending from 0 to approximately 20, where lower numbers denote more lipophilic and hydrophobic substances, and higher numbers denote more hydrophilic and lipophobic substances. The affinity of a compound for water, or for oily substances, is determined and its HLB value is assigned experimentally. The HLB of the hydrophobic carrier employed herein preferably will be in a range of about 13 to about 18.

A variety of pharmaceutically acceptable lipoidic agents may be incorporated in the formulation. The quantity of lipoidic agent present in the formulation is preferably at least 5 wt %, at least 15 wt %, at least 35 wt %, at least 40 wt % or at least 45 wt %. Suitable ranges include about 5 wt % to about 60 wt %, about 20 wt % to about 60 wt % and about 40 wt % to about 50 wt %.

In one embodiment, the lipoidic agent is a lipophilic emulsifier which has an HLB of less than 7 and comprises a member selected from the group consisting of mixed fatty acid monoglycerides; mixed fatty acid diglycerides; mixtures of fatty acid mono- and diglycerides; lipophilic polyglycerol esters; glycerol esters including glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan esters including sorbitan monostearate, sorbitan sesquioleate; fatty acids and their soaps including stearic acid, palmitic acid, and oleic acid; and mixtures thereof glyceryl monooleate, glyceryl dioleate, glyceryl monostearate, glyceryl distearate, glyceryl monopalmitate, and glyceryl dipalmitate; glyceryl-lacto esters of fatty acids; propylene glycol esters including propylene glycol monopalmitate, propylene glycol monostearate, and propylene glycol monooleate; sorbitan esters including sorbitan monostearate, sorbitan sesquioleate; fatty acids and their soaps including stearic acid, palmitic acid, and oleic acid; and mixtures thereof.

A preferred lipoidic agent is selected from glycerides and derivatives thereof. Preferred glycerides are selected from the group consisting of medium or long chain glycerides, caprylocaproyl macrogolglycerides, and mixtures thereof.

Preferred medium chain glycerides include, but are not limited to, medium chain monoglycerides, medium chain diglycerides, caprylic/capric triglyceride, glyceryl monolaurate, glyceryl monostearate, caprylic/capric glycerides, glycerylmonocaprylate, glyceryl monodicaprylate, caprylic/capric linoleic triglyceride, and caprylic/capric/succinic triglyceride.

Monoglycerides having a low melting point are preferred for making the formulation. Preferred monoglycerides include but are not limited to, glyceryl monostearate, glyceryl monopalmitate, glyceryl monooleate, glyceryl monocaprylate, glyceryl monocaprate, glyceryl monolaurate, etc., preferably glyceryl monostearate (GMS). GMS is a natural emulsifying agent. It is oil soluble, but poorly soluble in water. GMS has an HLB value of 3.8. Another preferred monoglyceride is glyceryl monooleate (GMO). GMO is also a natural emulsifying agent; it is oil soluble, but poorly soluble in water, and it has an HLB value of 3.8.

In another embodiment, the glyceride is an absorption enhancer selected from caprylocaproyl macrogolglycerides. Caprylocaproyl macrogolglycerides which may be employed include, but are not limited to, polyethylene glycosylated glycerides, also known as polyglycolized glycerides or PEGylated glycerides. PEGylaed glycerides which may be employed in the composition include, but are not limited to, mixtures of monoglycerides, diglycerides, and triglycerides and monoesters and diesters of polyethylene glycol, polyethylene glycosylated almond glycerides, polyethylene glycosylated corn glycerides, and polyethylene glycosylated caprylic/capric triglyceride. The absorption enhancer preferably has an HLB value from 13 to 18, more preferably from 13 to 15.

One preferred absorption enhancer is known under the trade name GELUCIRE, and is commercially available from Gattefosse Corporation, Paramus, N.J., USA. GELUCIRE is a well known excipient which is a family of fatty acid esters of glycerol and PEG esters, also known as polyglycolized glycerides. GELUCIRE is used in various applications including preparing sustained release pharmaceutical compositions. GELUCIRE compounds are inert, semi-solid waxy materials which are amphiphilic and are available with varying physical characteristics such as melting point, HLB, and solubilities in various solvents. They are surface active in nature and disperse or solubilize in aqueous media forming micelles, microscopic globules or vesicles. They are identified by their melting point/HLB value. The melting point is expressed in degrees Celsius. One or a mixture of different grades of GELUCIRE excipient may be chosen to achieve the desired characteristics of melting point and/or HLB value.

The preferred GELUCIRE composition is GELUCIRE 44/14, a semisolid waxy material with a melting point of 44° C. and a HLB of 14.

Another preferred polyglycolyzed glyceride absorption enhancer is caprylocaproyl macrogol-8-glyceride (CAS No. 85536-07-8 and 84963-88-2). This is a mixture of mono-, di- and triesters of glycerol and of PEG 400 with medium-chain fatty acids ($C_8$-$C_{10}$) which is marketed, for example, by Gattefossé Corporation, Paramus, N.J., USA under the trade name LABRASOL. LABRASOL has a HLB value of 14 and has the following composition by weight: $C_8$-$C_{10}$ monoglycerides approximately 4%; $C_8$-$C_{10}$ diglycerides approximately 17%; $C_8$-$C_{10}$ triglycerides approximately 6%; $C_8$-$C_{10}$ monoesters of PEG 400 approximately 14%; $C_8$-$C_{10}$ diesters of PEG 400 approximately 36%; free PEG 400 approximately 20%; free glycerol approximately 3%.

Preferably, the lipoidic agent includes a mixture of a lipophilic emulsifier which has an HLB of less than 7 and an absorption enhancer that preferably has an HLB value from 13 to 18. The lipophilic emulsifier is preferably present in an amount in a range of about 20 wt % to about 50 wt %, preferably about 30 wt % to about 40 wt %, and the absorption enhancer is preferably present in an amount of about 5 to about 20 wt %, preferably about 8 to about 15 wt %.

The low melting points of many of the solid lipoidic compositions provide a means of incorporating the pharmaceutically active ingredients in them at temperatures from about 0° C. to about 50° C. above their respective melting points, and then filling the melt (solution and/or dispersion) in animal or vegetable gelatin capsules. The melt solidifies inside the capsules upon cooling to room temperature.

The oily component serves as a vehicle, preferably the main vehicle, for the vitamin D compound. Any pharmaceutically-acceptable oil can be used. Examples include animal (e.g., fish), vegetable (e.g., soybean), and mineral oils. The oil preferably will readily dissolve the vitamin D compound used. Preferred oily components include non-digestible oils, such as mineral oils, particularly liquid paraffins, and squalene. The oil vehicle preferably comprises about 10 wt % to about 50 wt % of the formulation, more preferably about 15 wt % to about 45 wt % about 20 wt % to about 40 wt %, or about 15 wt % to about 25 wt %. In one preferred embodiment, the liquid paraffin can be characterized by one or more of the following parameters: specific gravity about 0.88 to 0.89; kinematic viscosity (40° C.) abut 64 to about 70 cSt; molecular weight 424; % paraffinic hydrocarbons about 59; and pour point—24° C. The ratio between the waxy component and the oily component can be optimized in order to achieve the desired rate of release of the vitamin D compound. Thus, if a heavier oil component is used, relatively less of the waxy component can be used, and if a lighter oil component is used, then relatively more waxy component can be used.

Any vitamin D compound suitable for prophylactic and/or therapeutic use, and combinations thereof, are contemplated for inclusion in the formulation described herein. Vitamin D, 25-hydroxyvitamin D, 1,25-dihydroxyvitamin D, and other metabolites and analogs of Vitamin D are also useful as active compounds in pharmaceutical compositions. Specific examples include, but are not limited to, Vitamin $D_3$ (cholecalciferol), Vitamin $D_2$ (ergocalciferol), 25-hydroxyvitamin $D_3$, 25-hydroxyvitamin $D_2$, 1α,25-dihydroxyvitamin $D_3$, 1α,25-dihydroxyvitamin $D_2$, 1α,25-dihydroxyvitamin $D_4$, and vitamin D analogs (including all hydroxy and dihydroxy forms), including 1,25-dihydroxy-19-nor-vitamin $D_2$, and 1α-hydroxyvitamin $D_3$. In one type of embodiment, the vitamin D compound includes one or more hydroxy forms, such as a combination of 25-hydroxyvitamin $D_3$ and 25-hydroxyvitamin $D_2$. In some embodiments, the vitamin D compound is administered in a therapeutically effective amount (e.g., amount effective to prevent or treat hypovitaminosis D and/or secondary hyperparathyroidism).

One aspect of the disclosure includes a composition comprising a controlled release formulation of cholecalciferol and/or ergocalciferol and a method of administering such a formulation (in one embodiment, in high doses) to treat 25-hydroxyvitamin D insufficiency and deficiency at a level of efficiency heretofore unobtainable; without adverse supraphysiological surges in intraluminal, intracellular and blood levels of cholecalciferol, ergocalciferol and 25-hydroxyvitamin D and their consequences; and without serious side effects associated with Vitamin D supplementation, namely Vitamin D toxicity.

The controlled release compositions are designed to contain concentrations of the cholecalciferol/ergocalciferol at or above the UL, and are prepared in such a manner as to effect controlled, preferably substantially constant, release of the cholecalciferol/ergocalciferol over an extended period of time. Elevating intraluminal, blood, or intracellular concentrations of either precursor increases prohormone production. Furthermore, the compositions optionally can be designed for delayed release into the ileum of the gastrointestinal tract of humans or animals. It is contemplated that in one type of embodiment the compositions will ensure a substantially constant concentration of cholecalciferol/ergocalciferol in the body and a more sustained blood level. By providing a slow and steady release of the cholecalciferol/ergocalciferol over time, blood, intraluminal and intracellular Vitamin D concentration spikes, i.e., adverse supraphysiologic levels, are mitigated or eliminated.

Compositions comprising Vitamin $D_3$ at a dose of greater than 5,000 IU, or greater than 7,500 IU, or greater than 10,000 IU are contemplated. Compositions comprising a combination of cholecalciferol and ergocalciferol at a unit dose of at least 1,500 IU (combined), or at least 2,000, 2,500, 3,000, 4,000, 5,000, 6,000, 7,000, 7,500, 8,000, 9,000, 10,000, 11,000, 12,000 or 12,500 IU are contemplated. Such unit doses less than 200,000 IU, or less than 100,000 or 75,000 or 50,000 IU are also contemplated.

The invention also contemplates that doses may be given at intervals of once a day, once every other day, three times a week, twice a week, weekly, or every 2 weeks. The cumulative dose taken each time may be 1,500 IU (cholecalciferol and ergocalciferol separately or combined), or at least 2,000, 2,500, 3,000, 4,000, 5,000, 6,000, 7,000, 7,500, 8,000, 9,000, 10,000, 11,000, 12,000 or 12,500 IU. Such doses less than 200,000 IU, or less than 100,000 or 75,000 or 50,000 IU are also contemplated. Such doses are preferred for use with adult humans.

The cholecalciferol and ergocalciferol can be included in any ratio, e.g., 9:1 to 1:9. Ratios including, but not limited to 1:1, greater than 1:1 cholecalciferol:ergocalciferol, and less than 1:1 cholecalciferol:ergocalciferol, are contemplated to be useful in various embodiments.

For example, a combination of 1,500 IU cholecalciferol and 1,500 IU ergocalciferol in a single unit dose capsule and/or in a daily dose is contemplated. Also contemplated are combinations of 1,000 IU cholecalciferol with 1,000 IU ergocalciferol in a single unit dose capsule and/or in a daily dose and 2,000 IU cholecalciferol with 2,000 IU ergocalciferol in a single unit dose capsule and/or in a daily dose. The initial dosing regimen of such a unit dose capsule can be based on baseline serum 25(OH)D (ng/ml) [nmol/L] levels, for example as detailed in Table 1 below for a combination of 1,500 IU cholecalciferol and 1,500 IU ergocalciferol in a single unit dose capsule.

TABLE 1

| Serum 25(OH)D (ng/ml) [nmol/L] | Description | Dose | Duration | Comment |
| --- | --- | --- | --- | --- |
| <5 [12] | severe vitamin D deficiency | 2 capsules daily | 8 weeks | measure 25(OH)D levels |
| 5-15 [12-37] | mild vitamin D deficiency | 2 capsules daily | 6 weeks | measure 25(OH)D levels |
| 16-30 [40-75] | vitamin D insufficiency | 2 capsules daily | 2 weeks | measure 25(HO)D levels |
| ≧30 [≧75] | vitamin D sufficiency | 1 capsule daily | continuous | measure 25(OH)D levels/6 months |

To maintain serum concentrations of 25(OH)D at 30 ng/mL or above, one such capsule can be administered per day to adult patients.

The invention also includes compositions comprising oral formulations of 25-hydroxyvitamin $D_2$ and/or 25-hydroxyvitamin $D_3$ ("25-hydroxyvitamin $D_2$/25-hydroxyvitamin $D_3$") and methods of administering such formulations to treat 25-hydroxyvitamin D insufficiency and deficiency without supraphysiological surges in intraluminal, intracellular and blood levels of 25-hydroxyvitamin D and their consequences; without causing substantially increased catabolism of the administered 25-hydroxyvitamin D; and, without causing serious side effects associated with Vitamin D supplementation, namely Vitamin D toxicity.

The controlled release compositions intended for oral administration in accordance with the invention preferably are designed to contain concentrations of the 25-hydroxyvitamin $D_2$/25-hydroxyvitamin $D_3$ of 1 to 1000 μg per unit dose and are prepared in such a manner as to effect controlled or substantially constant release of the 25-hydroxyvitamin $D_2$/25-hydroxyvitamin $D_3$, optionally into the ileum of the gastrointestinal tract, of humans or animals over an extended period of time. Preferred dosages include 1 to 1000 μg per unit dose, 1 to 600 μg, 1 to 400 μg, 1 to 200 μg, 1 to 100 μg, 5 to 90 μg, 30 to 80 μg, 20 to 60 μg, 30 to 60 μg, 35 to 50 μg, 5 to 50 μg, and 10 to 25 μg, for example 20 μg, 25 μg, 30 μg, 40 μg, 50 μg, 60 μg, 70 μg, 80 μg, 90 μg, and 100 μg. The compositions may provide substantially increased absorption of 25-hydroxyvitamin D via transport on DBP and decreased absorption via transport in chylomicrons. The compositions may provide maintenance of substantially constant blood levels of 25-hydroxyvitamin D during the 24-hour post-dosing period. By providing a gradual, sustained and direct release of the 25-hydroxyvitamin $D_2$/25-hydroxyvitamin $D_3$ and absorption preferentially to circulating DBP (rather than to chylomicrons), blood, intraluminal and intracellular 25-hydroxyvitamin D concentration spikes, i.e., supraphysiologic levels and related unwanted catabolism can be mitigated or eliminated. Furthermore, by providing a gradual and sustained release, serum levels of 25-hydroxyvitamin D can be increased and maintained more predictably than by administration of immediate release oral formulations, allowing for a consistent dosage and reducing or eliminating the need for frequent patient monitoring.

In one preferred class of embodiments, the modified release formulation releases at least 70%, more preferably at least 80% of the vitamin D compound within the first 24 hours after dosing, for example about 72%.

Advantageously, 25-hydroxyvitamin $D_2$, 25-hydroxyvitamin $D_3$ or combinations thereof together with other therapeutic agents can be orally or intravenously administered in accordance with the above described embodiments in dosage amounts of from 1 to 100 µg per day, with the preferred dosage amounts of from 5 to 50 µg per day, for example about 10 to 25 µg. Preferred doses will provide an average rise in serum 25-hydroxyvitamin $D_3$ of about 1 to 3 ng/mL.

In embodiments, the method is contemplated to include administering a formulation described herein to raise and preferably also maintain blood 1,25-dihydroxyvitamin D levels at 25 pg/mL, 30 pg/mL, or higher, e.g. 25-65 pg/mL for an extended period, for example at least one month, at least three months, at least six months, or longer.

In one aspect, a method for lowering or maintaining lowered serum parathyroid hormone in human patients includes administering to said patients an effective amount of an active vitamin D hormone such as 1,25-dihydroxyvitamin $D_2$ according to the disclosure herein to lower or maintain lowered serum parathyroid hormone levels, preferably an amount that lowers PTH levels by at least 30%, or alternatively the amount needed to reduce serum levels of PTH to the target range for the CKD stage (e.g., for Stage 3 is 35-70 pg/mL (equivalent to 3.85-7.7 pmol/L), for Stage 4 is 70-110 pg/mL (equivalent to 7.7-12.1 pmol/L), and for Stage 5 is 150-300 pg/mL (equivalent to 16.5-33.0 pmol/L) (defined in K/DOQI Guideline No. 1)).

In another aspect, the method includes administering to a patient suffering from hyperparathyroidism secondary to chronic kidney disease (Stage 3, 4 or 5) an effective amount of an active vitamin D hormone such as 1,25-dihydroxyvitamin $D_2$ according to the disclosure herein to lower the serum PTH level.

The dosage of a 1,25-dihydroxyvitamin D for oral administration generally is about 0.1 µg per week to 100 µg per week, preferably about 0.7 µg per week to about 70 µg per week, which can be split into daily or other periodic doses, such as three times per week for administration concomitant with hemodialysis. In exemplary embodiments, an oral dosage equivalent to about 1, 2, 3, 4, 5, 6, 7, 8 or 9 µg per day is contemplated.

Generally, a 1,25-dihydroxyvitamin D compound is dispensed by unit dosage form comprising about 0.1 µg to about 10 µg per unit dosage, for example about 1 µg to about 4 µg, about 2 µg to about 10 µg, or about 3 µg to about 5 µg.

Administration of a vitamin D hormone, such as 1,25-dihydroxyvitamin $D_2$, as described herein also allows for the efficient and predictable delivery of a predetermined dosage of vitamin D hormone to a patient. The temporal and quantitative availability of the active vitamin D hormone is not dependent on activation in the liver or other metabolism. Accordingly, lower dosages, compared to delivery by other means, are considered possible in order to achieve equivalent effects, while optionally or preferably avoiding or reducing side effects, as described above.

The dosages described herein are contemplated for any of the therapeutic methods described herein. It will be appreciated that the actual preferred amount of a vitamin D compound in a specific case will vary according the particular compositions formulated, the mode of application, and the particular situs being treated. Dosages can be determined using conventional considerations, e.g., by customary comparison of the differential activity of the hormone and of a known agent, e.g. by means of an appropriate conventional pharmacological protocol.

The specific doses for each particular patient can depend on a wide variety of factors, for example, on the age, body weight, general state of health, sex, on the diet, on the timing and mode of administration, on the rate of excretion, and on medicaments used in combination and the severity of the particular disorder to which the therapy is applied.

Patients in need of vitamin D supplementation include healthy subjects and subjects at risk for vitamin D insufficiency or deficiency, for example, subjects with Stage 1, 2, 3, 4 or 5 CKD; infants, children and adults that do not drink vitamin D fortified milk (e.g. lactose intolerant subjects, subjects with milk allergy, vegetarians who do not consume milk, and breast fed infants); subjects with rickets; subjects with dark skin (e.g., in the U.S., 42% of African American women between 15 and 49 years of age were vitamin D deficient compared to 4% of white women); the elderly (who have a reduced ability to synthesize vitamin D and also are more likely to stay indoors); institutionalized adults (who are likely to stay indoors, including subjects with Alzheimer's disease or mentally ill); subjects who cover all exposed skin (such as members of certain religions or cultures); subjects who always use sunscreen (e.g., the application of sunscreen with a Sun Protection Factor (SPF) value of 8 reduces production of vitamin D by 95%, and higher SPF values may further reduce vitamin D); subjects with fat malabsorption syndromes (including but not limited to cystic fibrosis, cholestatic liver disease, other liver disease, gallbladder disease, pancreatic enzyme deficiency, Crohn's disease, inflammatory bowel disease, sprue or celiac disease, or surgical removal of part or all of the stomach and/or intestines); subjects with inflammatory bowel disease; subjects with Crohn's disease; subjects who have had small bowel resections; subjects with gum disease; subjects taking medications that increase the catabolism of vitamin D, including phenyloin, fosphenyloin, phenobarbital, carbamazepine, and rifampin; subjects taking medications that reduce absorption of vitamin D, including cholestyramine, colestipol, orlistat, mineral oil, and fat substitutes; subjects taking medications that inhibit activation of vitamin D, including ketoconazole; subjects taking medications that decrease calcium absorption, including corticosteroids; subjects with obesity (vitamin D deposited in body fat stores is less bioavailable); subjects with osteoporosis; and/or postmenopausal women. According to the Institute of Medicine's report on the Dietary Reference Intakes for vitamin D, food consumption data suggest that median intakes of vitamin D for both younger and older women are below current recommendations; data suggest that more than 50% of younger and older women are not consuming recommended amounts of vitamin D.

Optionally excluded from the methods of the invention described herein are therapeutic treatment of subjects suffering from renal osteodystrophy (including osteomalacia and osteitis fibrosa cystica).

In other aspects, the compositions and methods of the invention are useful for prophylactic or therapeutic treatment of vitamin D-responsive diseases, i.e., diseases where vitamin D, 25-hydroxyvitamin D or active vitamin D (e.g., 1,25-dihydroxyvitamin D) prevents onset or progression of disease, or reduces signs or symptoms of disease. Such vitamin D-responsive diseases include cancer (e.g., breast, lung, skin, melanoma, colon, colorectal, rectal, prostate and bone cancer). 1,25-dihydroxyvitamin D has been observed to induce cell differentiation and/or inhibit cell proliferation in vitro for a number of cells. Vitamin D-responsive diseases also include autoimmune diseases, for example, type I diabetes, multiple sclerosis, rheumatoid arthritis, polymyositis, dermatomyositis, scleroderma, fibrosis, Grave's disease, Hashimoto's disease, acute or chronic transplant rejection, acute or chronic graft versus host disease, inflammatory bowel disease, Crohn's disease, systemic lupus erythematosis, Sjogren's Syndrome, eczema and psoriasis, dermatitis, including atopic dermatitis, contact dermatitis, allergic dermatitis and/or chronic dermatitis. Vitamin D-responsive diseases also include other inflammatory diseases, for example, asthma, chronic obstructive pulmonary disease, polycystic kidney disease, polycystic ovary syndrome, pancreatitis, nephritis, hepatitis, and/or infection. Vitamin D-responsive diseases have also been reported to include hypertension and cardiovascular diseases. Thus, the invention contemplates prophylactic or therapeutic treatment of subjects at risk of or suffering from cardiovascular diseases, for example, subjects with atherosclerosis, arteriosclerosis, coronary artery disease, cerebrovascular disease, peripheral vascular disease, myocardial infarction, myocardial ischemia, cerebral ischemia, stroke, congestive heart failure, cardiomyopathy, obesity or other weight disorders, lipid disorders (e.g. hyperlipidemia, dyslipidemia including associated diabetic dyslipidemia and mixed dyslipidemia hypoalphalipoproteinemia, hypertriglyceridemia, hypercholesterolemia, and low HDL (high density lipoprotein)), metabolic disorders (e.g. Metabolic Syndrome, Type II diabetes mellitus, Type I diabetes mellitus, hyperinsulinemia, impaired glucose tolerance, insulin resistance, diabetic complication including neuropathy, nephropathy, retinopathy, diabetic foot ulcer and cataracts), and/or thrombosis.

Diseases which can benefit from a modulation in the levels of vitamin D compounds, include, but are not limited to: (i) in the parathyroid—hypoparathyroidism, Pseudohypo-parathyroidism, secondary hyperparathyroidism; (ii) in the pancreas—diabetes; (iii) in the thyroid—medullary carcinoma; (iv) in the skin—psoriasis; wound healing; (v) in the lung—sarcoidosis and tuberculosis; (vi) in the kidney—chronic kidney disease, hypophosphatemic VDRR, vitamin D dependent rickets; (vii) in the bone—anticonvulsant treatment, fibrogenisis imperfecta ossium, osteitis fibrosa cystica, osteomalacia, osteoporosis, osteopenia, osteosclerosis, renal osteodytrophy, rickets; (viii) in the intestine—glucocorticoid antagonism, idopathic hypercalcemia, malabsorption syndrome, steatorrhea, tropical sprue; and (ix) autoimmune disorders.

In embodiments of the invention, the disease that benefits from a modulation in the levels of vitamin D compounds are selected from cancer, dermatological disorders (for example psoriasis), parathyroid disorders (for example hyperparathyroidism and secondary hyperparathyroidism), bone disorders (for example osteoporosis) and autoimmune disorders.

The formulation can be prepared by procedures well known to one of ordinary skill in the art. Typically, the pharmaceutically acceptable waxes, lipoidic agents, and oils are melted, if necessary, to provide a flowable liquid thereby making it easier to obtain a homogeneous mixture. The Vitamin D compound is added to the thus liquid carrier, for example dissolved in an alcohol such as anhydrous ethanol, and the ingredients are mixed to provide a homogeneous mixture. The mixture can be cooled and stored prior to later division into unit dosage forms, such as filled gelatin capsules.

In one preferred method, a portion of the oil vehicle, solid wax, and a lipophilic emulsifier are heated to a relatively high temperature (e.g., 65° C.) and mixed prior to adding an absorption enhancer, followed by additional mixing until homogenous, then cooling to an intermediate elevated temperature (e.g., 50° C. to 55° C.). In a separate vessel, an antioxidant preservative and the remainder of the oil vehicle are mixed and heated to an intermediate elevated temperature (e.g., 50° C.), then combined and mixed with the wax mixture until a homogenous solution is obtained. Next, a solution of vitamin D compound in alcohol is combined with the homogenous waxy solution, mixed until a homogenous solution is obtained, preferably filled into capsules, and then cooled to room temperature. In another preferred method, a portion of the oil vehicle, solid wax, and a lipophilic emulsifier are heated at a temperature of 55° C. to 60° C. and mixed prior to adding an absorption enhancer, followed by additional mixing until homogenous. In a separate vessel, an antioxidant preservative and the remainder of the oil vehicle are mixed and heated to a temperature of 55° C. to 60° C., then combined and mixed with the wax mixture until a homogenous solution is obtained. Next, a solution of vitamin D compound in alcohol is combined with the homogenous waxy solution, mixed until a homogenous solution is obtained, preferably filled into capsultes, and then cooled to room temperature.

The formulation preferably is placed in capsules prior to administration to the patient in need of treatment. Such capsules may be hard or soft, and soft capsules are preferred. The formulation may be filled into gelatin capsules using standard capsule filling machinery, such as by melting the formulation and injection filling it into soft capsule shells.

The formulation and methods of use and making are contemplated to include embodiments including any combination of one or more of the additional optional elements, features, and steps further described below, unless stated otherwise.

Thus, in one type of embodiment, the formulation further includes a preservative, such as an antioxidant. Butylated hydroxytoluene (BHT) is preferred.

In another type of embodiment, the vitamin D compound is administered in combination with one or more other therapeutic agents.

If the vitamin D compound is administered in combination with one or more other therapeutic agents, the proportions of each of the compounds in the combination being administered will be dependent on the particular disease state being addressed. For example, one may choose to orally administer 25-hydroxyvitamin $D_2$ and/or 25-hydroxyvitamin $D_3$ with one or more calcium salts (intended as a calcium supplement or dietary phosphate binder), bisphosphonates, calcimimetics, nicotinic acid, iron, phosphate binders, cholecalciferol, ergocalciferol, active Vitamin D sterols, glycemic and hypertension control agents, various antineoplastic agents and inhibitors of CYP24 and other cytochrome P450 enzymes that can degrade vitamin D agents. In addition, one may choose to intravenously administer 25-hydroxyvitamin $D_2$ and/or 25-hydroxyvitamin $D_3$ with cholecalciferol, ergocalciferol, active Vitamin D sterols, glycemic and hypertension control agents, various antineoplastic agents and inhibitors of CYP24 and other cytochrome P450 enzymes that can degrade vitamin D agents. In practice, higher doses of the compounds of the present invention are used where therapeutic treatment of a disease state is the desired end, while the lower doses are generally used for prophylactic purposes, it being understood that the specific dosage administered in any given case will be adjusted in accordance with the specific compounds being administered, the disease to be treated, the condition of the subject and the other relevant medical facts that may modify the activity of the drug or the response of the subject, as is well known by those skilled in the art.

As described above, the formulation is preferably filled into gelatin capsules, but it may also be administered in neat form, or with one or more external coating layers, such as an enteric coating. It is also contemplated that the formulation can be pressed into tablets, and in such cases one or more tablet pressing excipients may be included.

In the compositions and methods described herein, preferred steps, preferred components, preferred compositional ranges thereof, and preferred combinations of the foregoing, can be selected from the various specific examples provided herein. For example, a preferred formulation includes 25-hydroxyvitamin D (e.g. 25-hydroxyvitamin $D_3$, for example about 0.1 wt % (e.g. 0.12 wt %)), about 2 wt % (e.g., 2.32 wt %) ethanol, about 10 wt % (e.g., 9.75 wt %) GELUCIRE 44/14, about 27 wt % (e.g., 27.51 wt. %) hard paraffin, about 38 wt % (e.g., 37.85 wt %) GMS, about 22 wt % (e.g., 22.43 wt %) mineral oil, and optionally a small amount of preservative (e.g., 0.02 wt % BHT). A variation on this formulation will include about 20% hard paraffin and about 29% mineral oil.

Specifications for still another preferred embodiment of a capsule, and a 50 μg embodiment, are shown in Table 2 below.

TABLE 2

| Ingredient | Milligram per capsule | % w/w |
|---|---|---|
| 25-hydroxyvitamin $D_3$ | 0.040 | 0.024 |
| Dehydrated ethanol | 4.22 | 2.48 |
| Hard Paraffin | 33.97 | 19.98 |
| Mineral Oil | 50.80 | 29.88 |
| GELUCIRE 44/14 | 16.59 | 9.76 |
| GMS | 64.35 | 37.85 |
| BHT | 0.034 | 0.020 |
| Total | 170.00 | 100.00 |

EXAMPLES

The following Examples illustrate specific formulations and methods for their preparation. The Examples are provided for illustration and are not intended to limit the scope of the invention.

Example 1

Modified Release Formulations

Nine oral vitamin D formulations were prepared according to Table 3 below by homogeneously mixing the identified components in the amounts shown and filling the mixtures into hard gelatin capsules. Formulation 9 is an immediate-release formulation according to the prior art, wherein MIGLYOL 812N is the trade name for caprylic/capric triglycerides, available from CONDEA Chemie GmbH of Cranford, N.J., USA. The formulations were administered to groups of Yucatan miniature swine (about 10 kg), in single doses equivalent to 250 μg of 25-hydroxyvitamin $D_3$. Each group included five animals. An equivalent 250 μg of 25-hydroxyvitamin $D_3$ was administered to a tenth group of five Yucatan miniature swine via intravenous injection.

TABLE 3

| | Ingredient | 25-(OH)-Vitamin $D_3$ | Ethanol | Carnauba Wax | GELUCIRE 44/14 | LABRASOL | Soybean Oil | BHT | Hard Paraffin | GMS | GMO | Liquid Paraffin | MIGLYOL 812N | Total |
|---|---|---|---|---|---|---|---|---|---|---|---|---|---|---|
| 1 | % w/w | 0.12 | 2.32 | 14.63 | 9.75 | 9.75 | 63.40 | 0.02 | | | | | | 100 |
|   | mg/Cap | 0.25 | 4.75 | 30.00 | 20.00 | 20.00 | 130.00 | 0.04 | | | | | | 205 |
| 2 | % w/w | 0.12 | 2.32 | 27.50 | 9.75 | 9.75 | 50.53 | 0.02 | | | | | | 100 |
|   | mg/Cap | 0.25 | 4.75 | 56.40 | 20.00 | 20.00 | 103.60 | 0.04 | | | | | | 205 |
| 3 | % w/w | 0.12 | 2.32 | 14.63 | 9.75 | 37.85 | 35.31 | 0.02 | | | | | | 100 |
|   | mg/Cap | 0.25 | 4.75 | 30.00 | 20.00 | 77.60 | 72.40 | 0.04 | | | | | | 205 |
| 4 | % w/w | 0.12 | 2.32 | 11.51 | 8.10 | 3.12 | 74.80 | 0.02 | | | | | | 100 |
|   | mg/Cap | 0.25 | 4.75 | 23.60 | 16.60 | 6.40 | 153.36 | 0.04 | | | | | | 205 |
| 5 | % w/w | 0.12 | 2.32 | | 9.75 | | | 0.02 | 14.63 | | 37.85 | 35.31 | | 100 |
|   | mg/Cap | 0.25 | 4.75 | | 20.00 | | | 0.04 | 30.00 | | 77.60 | 72.40 | | 205 |
| 6 | % w/w | 0.12 | 2.32 | | 9.75 | | | 0.02 | 14.63 | 9.75 | 9.75 | 53.65 | | 100 |
|   | mg/Cap | 0.25 | 4.75 | | 20.00 | | | 0.04 | 30.00 | 20.00 | 20.00 | 110.00 | | 205 |
| 7 | % w/w | 0.12 | 2.32 | | 9.75 | | | 0.02 | 27.51 | 37.85 | | 22.43 | | 100 |
|   | mg/Cap | 0.25 | 4.75 | | 20.00 | | | 0.04 | 56.40 | 77.60 | | 46.00 | | 205 |
| 8 | % w/w | 0.12 | 2.32 | | | | | 0.02 | 9.75 | 9.75 | 9.75 | 68.23 | | 100 |
|   | mg/Cap | 0.25 | 4.75 | | | | | 0.04 | 20.00 | 20.00 | 20.00 | 139.96 | | 205 |
| 9 | % w/w | 0.12 | 2.32 | | | | | 0.02 | | | | | 97.54 | 100 |
|   | mg/Cap | 0.25 | 4.75 | | | | | 0.04 | | | | | 199.96 | 205 |

Blood was collected pre-dose, and at 0.5, 1, 2, 4, 6, 8, 12, 24, 48, 96, 168, 240, 336, 432, 504, 576, and 672 hours post dosing. Serum 25-hydroxyvitamin $D_3$ levels were assayed by Liquid Chromatography/Mass Spectrometry/Mass Spectrometry (LC MS/MS).

Plots of the change in serum 25-hydroxyvitamin $D_3$ levels over the first 24 hours for Groups 1-8 are shown in FIG. 1 through FIG. 8. In addition, the data for the Group 9 immediate release control are plotted with the Group 7 data in FIG. 7. The concentration profiles show that the Group 7 formulation according to the invention (a) produced a gradually increasing and sustained rise in serum 25-hydroxyvitamin $D_3$ levels over the first 24 hours, and (b) avoided a surge in 25-hydroxyvitamin $D_3$ levels.

Figure 9:
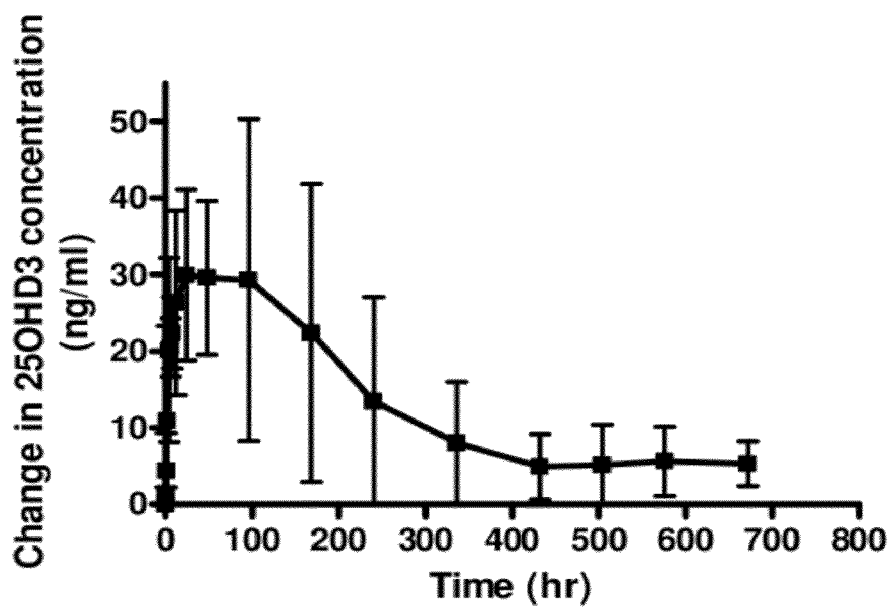
FIG. 9 through FIG. 11 show plots of the change in serum 25-hydroxyvitamin $D_3$ levels over the period of the study of Example 1 for the Group 7 controlled release formulation according to the invention, the Group 9 immediate release formulation according to the prior art, and Group 10 intravenous administration.
Figure 10:
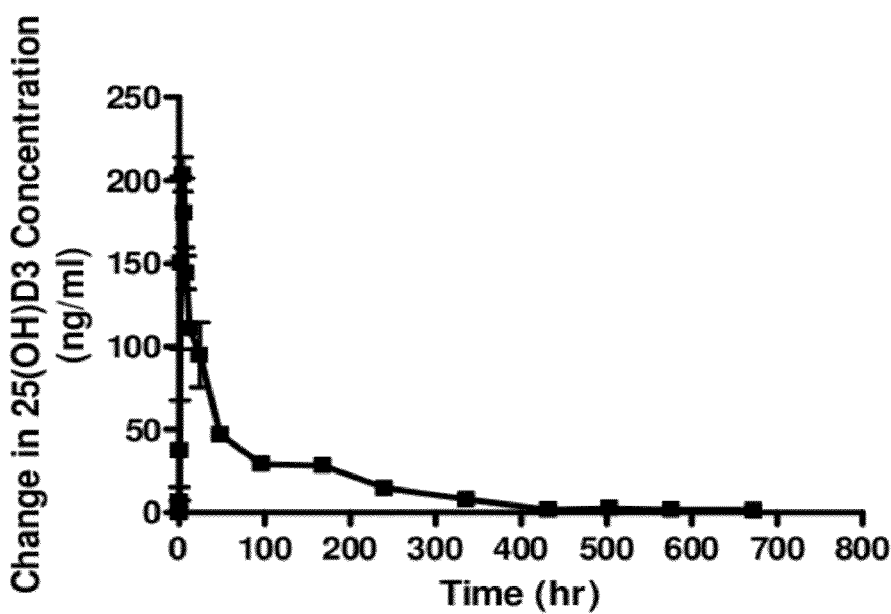
Figure 11:
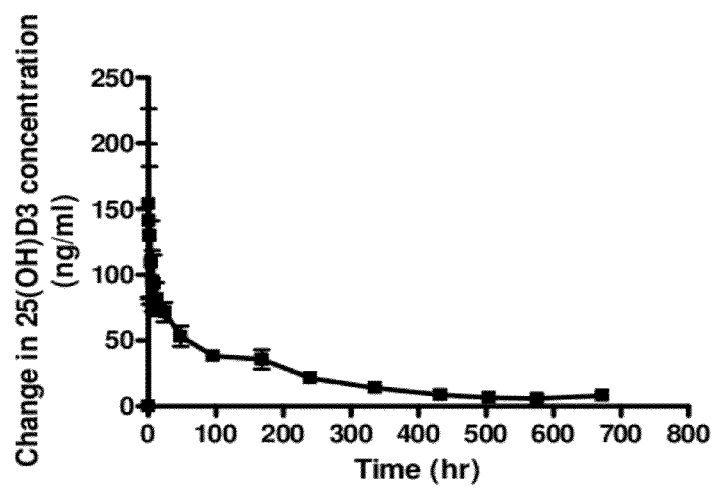
Figure 12:
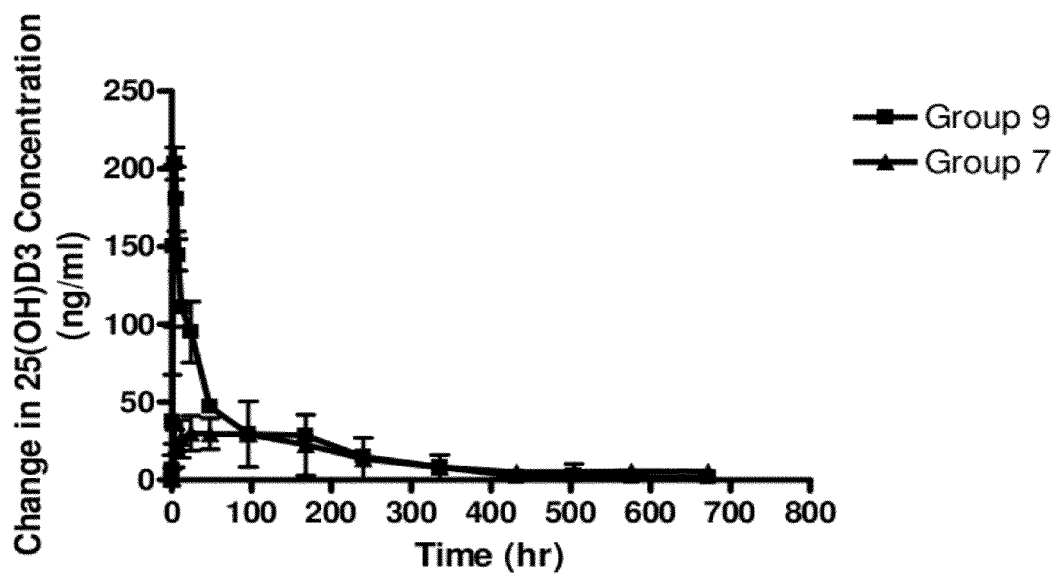
FIG. 12 shows an overlay plot of the data in FIG. 9 and FIG. 10 for Groups 7 and 9, respectively, in Example 1.
Figure 13:
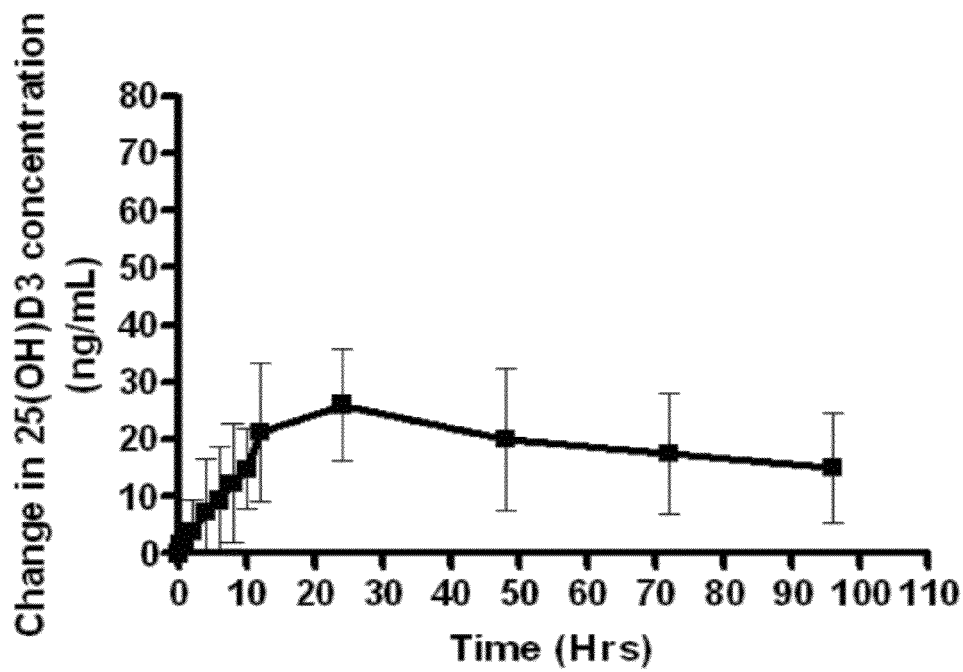
FIG. 13 through FIG. 18 show mean pharmacokinetic profile for miniature swine dosed with modified and immediate release oral formulations of 25-hydroxyvitamin $D_3$ according to Example 2.
Figure 14:
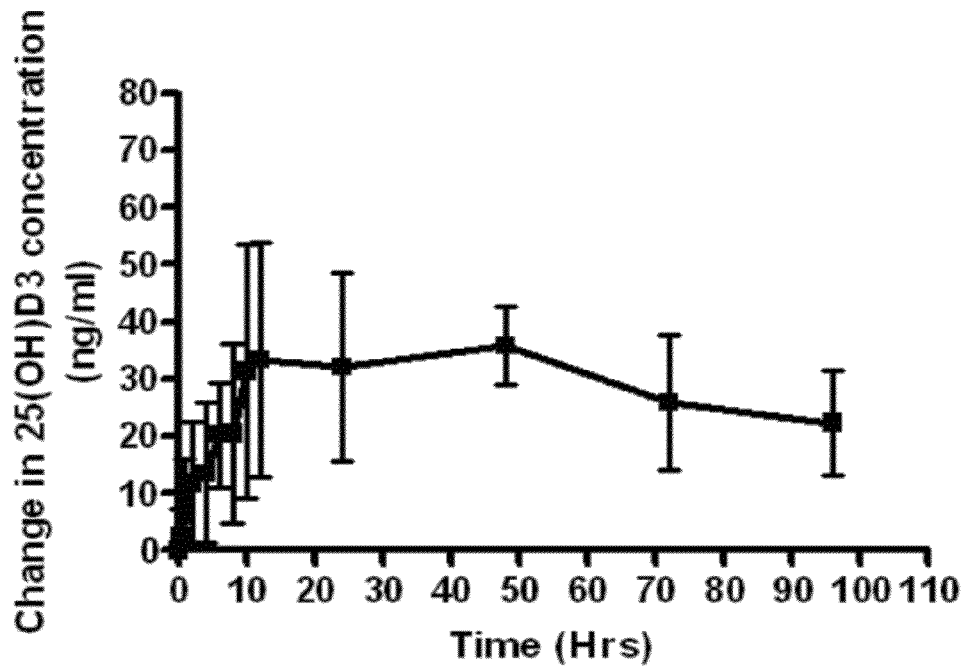
Figure 15:
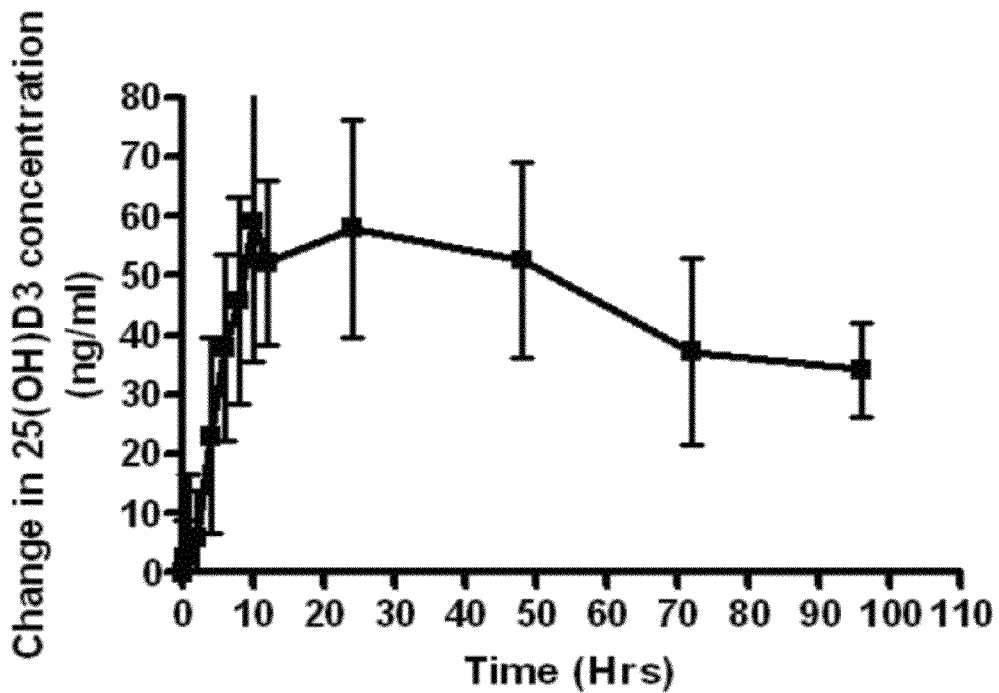
Figure 16:
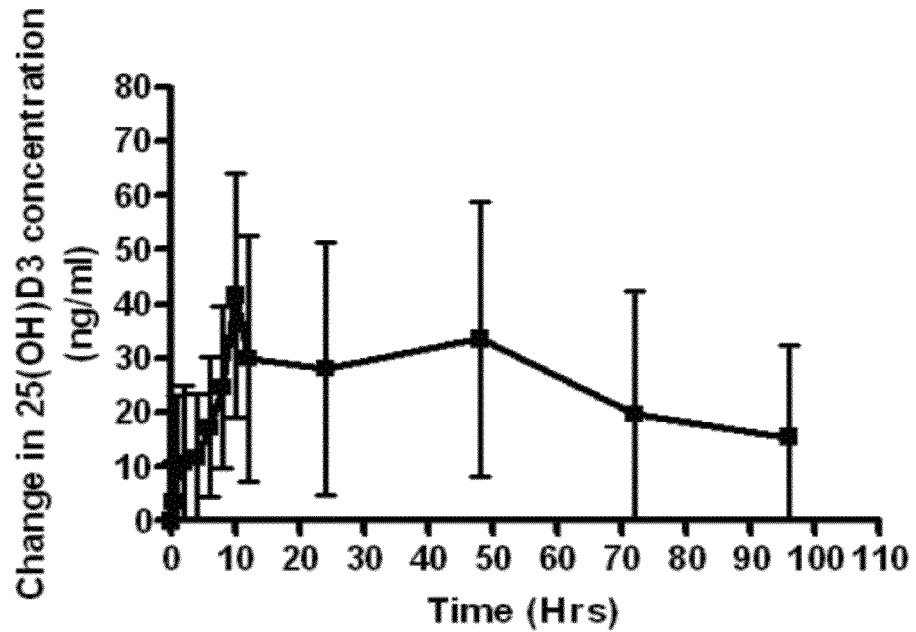
Figure 17:
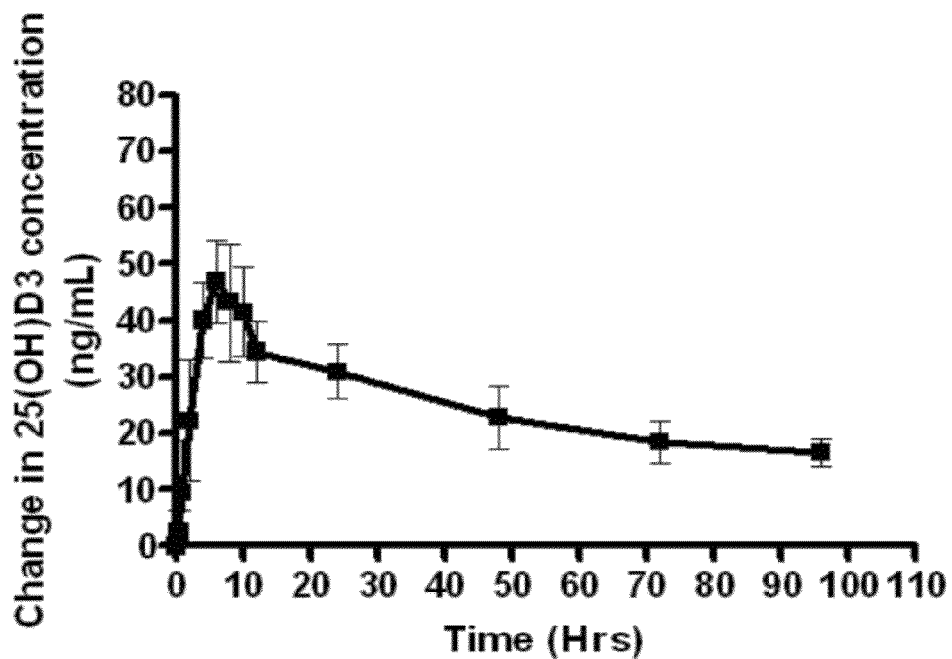
Figure 18:
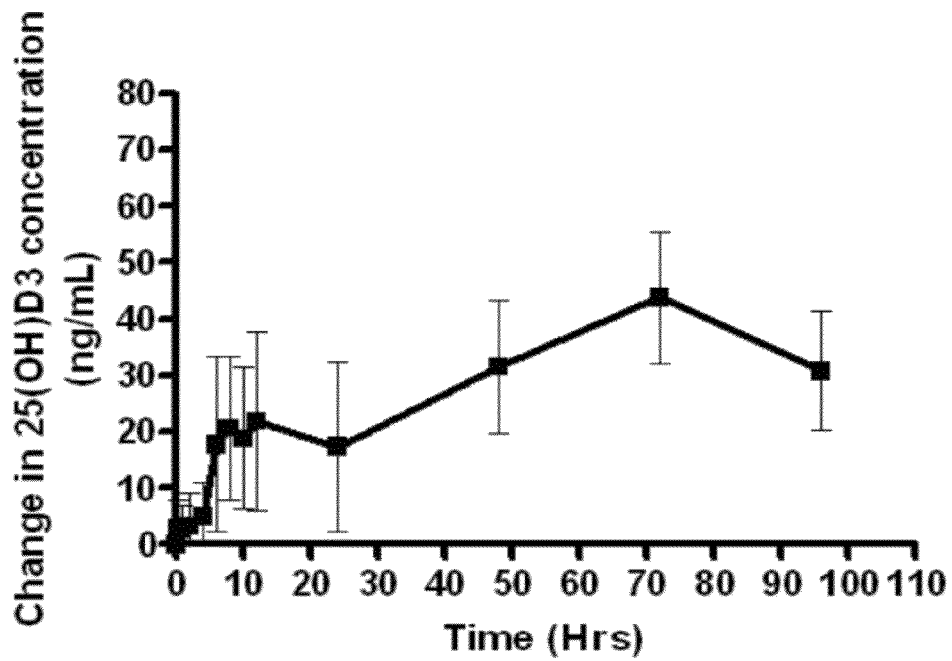

FIG. 9 through FIG. 11 show plots of the change in serum 25-hydroxyvitamin $D_3$ levels over the period of the study for Groups 7, 9, and 10, respectively. FIG. 12 shows an overlay plot of the data in FIG. 9 and FIG. 10 for Groups 7 and 9, respectively.

The concentration profiles shows that the Group 7 formulation according to the invention produced a gradually increasing rise in serum 25-hydroxyvitamin $D_3$ levels, avoided a surge in 25-hydroxyvitamin $D_3$ levels, and produced a sustained increase of serum 25-hydroxyvitamin $D_3$ over a long period of time.

In vitro dissolution tests of the same formulations (dissolution media: 0.056 lipase in Ctab/NaH$_2$PO$_4$ buffer, pH 6.8) over a period of 120 minutes showed results generally consistent with the in vivo data (e.g., formulations 2 and 7 showed a more gradual and incomplete rise in % dissolution, whereas the immediate release control showed 100% release within 30 minutes).

The data in Table 4 below show various pharmacokinetic parameters produced in the test subjects by administration of the Group 7 formulation according to the invention compared to the Group 9 prior art immediate release formulation and the Group 10 IV injection administration. The data demonstrate that the Group 7 formulation according to the invention avoided a concentration spike, provided a maximum concentration at a time much later than the immediate release dosage form and the intravenous injection, and provided a longer clearance half life than the comparable immediate release dosage form. The Group 7 formulation according to the invention resulted in a slower elimination of the 25-hydroxyvitamin $D_3$ administered from systemic circulation compared to Group 9.

A single dose of 250 μg 25-hydroxyvitamin $D_3$ administered according to the Group 7 formulation of the invention to mini-pigs (about 10 kg) resulted in an approximately 40 ng/ml rise in serum 25-hydroxyvitamin $D_3$. A single dose of 50 μg 25-hydroxyvitamin $D_3$ to a human (about 60 kg) is expected to increase serum levels of 25-hydroxyvitamin $D_3$ by about 1.4 ng/ml.

TABLE 4

| Grp | | AUC (0-672 hr) (ng/ml hr) | AUC (0-INF) (ng/ml hr) | Cmax (ng/ml) | Tmax (hr) | T½ (hr) | $Cmax_{24hr}/C_{24hr}$ (ng/ml) | BA (%) |
|---|---|---|---|---|---|---|---|---|
| 7 | AVG | 8062.6 | 10425.7 | 39.5 | 39.2 | 120.9 | 1.42 | |
| | STD | 6259.2 | 6676.4 | 11.4 | 35.4 | 27.9 | 0.93 | 62.7 |
| | % RSD | 77.63 | 64.0 | 28.7 | 90.2 | 23.0 | 65.41 | |
| 9 | AVG | 12074.5 | 12201.4 | 204.8 | 3.5 | 71.5 | 2.23 | |
| | STD | 1028.0 | 1099.0 | 12.6 | 1.0 | 16.9 | 0.49 | 73.4 |
| | % RSD | 8.5 | 9.0 | 6.1 | 28.6 | 23.7 | 22.11 | |
| 10 | AVG | 15038.0 | 16616.1 | 154.9 | 1.5 | 132.4 | 2.12 | |
| | STD | 2903.4 | 3646.2 | 71.1 | 1.7 | 18.7 | 0.84 | 100.0 |
| | % RSD | 19.3 | 21.9 | 45.9 | 112.0 | 14.1 | 39.67 | |

Comparative Cmax, Tmax, and bioavailability data for the formulations of Groups 1-6 and 8 are shown in Table 5 below.

TABLE 5

| Group | | $C_{max}$ (ng/ml) | $T_{max}$ (hr) | BA (%) |
|---|---|---|---|---|
| 1 | AVG | 105.9 | 7.0 | 69.1 |
| | STDEV | 33.0 | 9.6 | |
| | % RSD | 31.2 | 137.0 | |
| 2 | AVG | 29.7 | 12.8 | 25.3 |
| | STDEV | 15.2 | 10.4 | |
| | % RSD | 51.2 | 80.9 | |
| 3 | AVG | 109.4 | 4.0 | 84.1 |
| | STDEV | 22.6 | 0.0 | |
| | % RSD | 20.6 | 0.0 | |
| 4 | AVG | 162.1 | 4.8 | 97.2 |
| | STDEV | 30.3 | 1.8 | |
| | % RSD | 18.7 | 37.3 | |
| 5 | AVG | 90.8 | 3.2 | 70.7 |
| | STDEV | 22.7 | 1.1 | |
| | % RSD | 24.9 | 34.2 | |
| 6 | AVG | 99.9 | 3.2 | 72.3 |
| | STDEV | 24.3 | 1.8 | |
| | % RSD | 24.4 | 55.9 | |
| 8 | AVG | 91.5 | 3.6 | 70.2 |
| | STDEV | 41.2 | 0.9 | |
| | % RSD | 45.0 | 24.8 | |

Example 2

Pharmacokinetic Studies in Miniature Swine with Oral Capsules

The purpose of the study was to assess the systemic absorption of 25-hydroxyvitamin $D_3$ in male Yucatan swine (~45 kg body weight) following the administration of: a) 1×250 μg 25-hydroxyvitamin $D_3$ modified release (MR) capsule, b) 2×250 μg MR capsules, c) 4×250 μg MR capsules, d) 1×1000 μg MR capsule, e) 1×250 μg immediate release (IR) 25-hydroxyvitamin $D_3$ capsule, and f) 1×250 μg MR capsule administered on 3 consecutive days.

The MR formulations were prepared based on the formulation of Example 1, Group 7, above. In the case of the 1000 μg MR capsule, the higher concentration of 25-hydroxyvitamin $D_3$ was offset by a relative decrease in ethanol.

To prepare the IR formulation 25-hydroxyvitamin $D_3$ (0.12% wt/wt; 250 μg per capsule) was dissolved in ethanol USP (2.32% wt/wt; soliblizer) and mixed with corn oil USP, (97.54% wt/wt; main vehicle) and butylated hydroxytoluene (0.02% wt/wt; antioxidant). The corn oil solution (205 mg) was filled into size 0 two piece hard gelatin capsules.

Eight male Yucatan miniature swine per group were each administered a dose based on the dosing schedule in Table 6 below. Blood was collected from animals prior to first dose and at 0.5, 1, 2, 4, 6, 8, 10, 12, 24, 48, 72, and 96 hrs following first dose. Animals in Group 6 were administered a second and third dose immediately following the collection of the 24 and 48 hr blood samples, respectively. 25-hydroxyvitamin $D_3$ was assayed in all the collected samples. Ionized calcium and total calcium were determined in samples collected from animals in Group 1 and Group 5 at the following time points: pre dose and at 0.5, 1, 2, 4, 6, 8, 10, 12, 24, 48, 72, and 96 hrs following first dose.

TABLE 6

| Group ID | Number/Gender of Animals | Dose Route | Dose/Animal |
|---|---|---|---|
| 1M | 8/male | Oral | 1 capsule × 250 μg, modified release |
| 2M | 8/male | Oral | 2 capsules × 250 μg, modified release |
| 3M | 8/male | Oral | 4 capsules × 250 μg, modified release |
| 4M | 8/male | Oral | 1 capsule × 1000 μg, modified release |
| 5M | 8/male | Oral | 1 capsule × 250 μg, immediate release |
| 6M | 8/male | Oral | 3 capsules × 250 μg, modified release |

25-hydroxyvitamin $D_3$ in swine serum was assayed using solid-phase extraction (SPE) with high performance liquid chromatography with tandem mass spectrometry (LC-MS/MS) detection. Serum samples were baseline corrected to exclude endogenous concentrations of 25-hydroxyvitamin $D_3$ from the pharmacokinetic analysis. To achieve this pre-dose 25-hydroxyvitamin $D_3$ concentration of each animal were subtracted from each of its post dose concentrations. Serum samples below the 1 ng/ml (lower limit of quantitation) were assigned a value of zero.

Pharmacokinetic parameters are reported in Table 7.

TABLE 7

| Group | | $AUC_{(0-24\,hr)}$ (ng/ml hr) | $AUC_{(0-t)}$ (ng/ml hr) | $C_{max}$ (ng/mL) | $C_{24\,hr}$ (ng/mL) | $T_{max}$ (hours) | $C_{max}/C_{24\,hr}$ | $C_{max}/AUC_{(0-24\,hr)}$ |
|---|---|---|---|---|---|---|---|---|
| 1 | AVG | 417.81 | 1838.73 | 31.58 | 26.08 | 26.50 | 1.28 | 0.08 |
|   | STDEV | 121.63 | 709.85 | 7.63 | 9.87 | 22.42 | 0.28 | 0.02 |
|   | % RSD | 29.1 | 38.6 | 24.1 | 37.9 | 84.6 | 22.0 | 29.3 |
| 2 | AVG | 619.30 | 2862.75 | 47.86 | 36.80 | 30.50 | 1.42 | 0.10 |
|   | STDEV | 315.95 | 528.10 | 14.51 | 10.86 | 23.24 | 0.38 | 0.08 |
|   | % RSD | 51.0 | 18.4 | 30.3 | 29.5 | 76.2 | 26.4 | 79.4 |
| 3 | AVG | 1059.99 | 4321.75 | 72.29 | 58.00 | 25.50 | 1.28 | 0.07 |
|   | STDEV | 232.36 | 894.26 | 18.76 | 18.35 | 23.22 | 0.27 | 0.008 |
|   | % RSD | 21.9 | 20.7 | 26.0 | 31.6 | 91.1 | 21.1 | 11.5 |
| 4 | AVG | 642.79 | 2608.04 | 52.19 | 39.41 | 25.71 | 1.61 | 0.12 |
|   | STDEV | 392.48 | 1574.53 | 20.41 | 15.97 | 20.89 | 0.35 | 0.08 |
|   | % RSD | 61.1 | 60.4 | 39.1 | 40.5 | 81.3 | 21.5 | 67.2 |
| 5 | AVG | 812.51 | 2374.50 | 49.73 | 30.97 | 5.75 | 1.63 | 0.06 |
|   | STDEV | 115.47 | 266.95 | 9.22 | 4.76 | 1.28 | 0.34 | 0.005 |
|   | % RSD | 14.2 | 11.2 | 18.5 | 15.4 | 22.3 | 21.0 | 8.7 |

Dose normalized pharmacokinetic parameters for Groups 1 to 3 are reported in Table 8.

TABLE 8

| PK Parameters | Group 1 | | | Group 2 | | | Group 3 | | |
|---|---|---|---|---|---|---|---|---|---|
| | AVG | STDEV | % RSD | AVG | STDEV | % RSD | AVG | STDEV | % RSD |
| $AUC_{(0-t)}$ (ng/ml hr)/μg | 7.35 | 2.84 | 38.61 | 5.73 | 1.06 | 18.45 | 4.32 | 0.89 | 20.69 |
| $C_{max}$ (ng/mL)/μg | 0.13 | 0.03 | 24.15 | 0.10 | 0.03 | 30.33 | 0.07 | 0.02 | 25.96 |
| $C_{24\,hr}$ (ng/mL)/μg | 0.10 | 0.04 | 37.85 | 0.07 | 0.02 | 29.50 | 0.06 | 0.02 | 31.64 |
| $AUC_{(0-24\,h)}$ (ng/ml hr)/μg | 1.67 | 0.49 | 29.11 | 1.24 | 0.63 | 51.02 | 1.06 | 0.23 | 21.92 |

For the groups administered 1, 2 and 4 capsules (250 μg MR capsules), there was an increase in exposure as a function of dose. Dose proportional exposure occurred at the 1×250 μg and 2×250 μg doses, while slightly less than proportional exposure was observed between 2×250 μg and 4×250 μg doses. The mean time at which maximum concentration was achieved ($T_{max}$) was between 25.5 to 30.5 hrs.

Comparison of exposure from a single capsule (1×1000 μg) versus four capsules (4×250 μg) indicated higher exposure in animals dosed with multiple capsules. Dose independent parameters, such as mean $T_{max}$, were similar for both dosing strategies.

The comparison of the modified release formulation of 25-hydroxyvitamin $D_3$ (MR) (Group 1) to the IR formulation (Group 5), indicated that the MR formulation avoided a spike in the concentration of serum 25-hydroxyvitamin $D_3$. The relative bioavailability of the MR formulation when compared to the IR formulation was approximately 77%. Animals receiving the MR formulation exhibited a mean $T_{max}$ of 26.5 hrs which indicated a significant delay compared to the animals receiving the IR formulation ($T_{max}$=5.75 hrs).

Exposure was assessed in animals receiving 1×250 μg MR capsules on Days 1, 2 and 3. The mean increase in concentration of 25-hydroxyvitamin $D_3$ over baseline 24 h following dosing was 17.3, 31.5 and 43.9 ng/mL following the first, second and third dose respectively.

Figure 19:
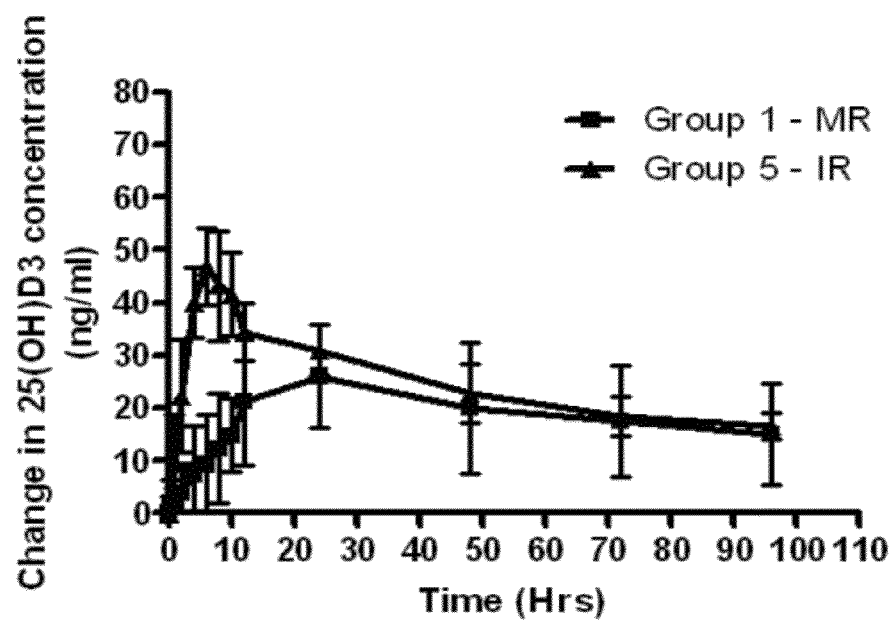
FIG. 19 shows a comparison of pharmacokinetic profiles for MR and IR formulations of 250 µg 25-hydroxyvitamin $D_3$ according to Example 2.

FIG. 13 through FIG. 18 show the mean pharmacokinetic profile for animals in Groups 1-6, respectively. FIG. 19 shows a comparison of pharmacokinetic profiles for MR and IR formulations of 250 μg 25-hydroxyvitamin $D_3$.

Example 3

Systemic Exposure Studies in Miniature Swine with Oral Capsules

The purpose of this study was to assess the increase in systemic 25-hydroxyvitamin $D_3$ concentrations in healthy normal male Yucatan swine (~50-60 kg body weight) maintained on a diet including an adequate intake of Vitamin D, following the daily administration of the following: a) 25 μg immediate release (IR) 25-hydroxyvitamin $D_3$ capsules (Group 1), b) 25 μg modified release (MR) 25-hydroxyvitamin $D_3$ capsules (Group 2), and c) 125 μg MR 25-hydroxyvitamin $D_3$ capsules (Group 3), for 21 days.

The MR formulations were prepared based on the formulation of Example 1, Group 7, above. The differences in concentration of 25-hydroxyvitamin $D_3$ were offset by relative changes in ethanol.

To prepare the IR formulation 25-hydroxyvitamin $D_3$ (0.12% wt/wt; 250 μg per capsule) was dissolved in ethanol USP (2.32% wt/wt; solublizer) and mixed with corn oil USP (97.54% wt/wt; main vehicle) and butylated hydroxytoluene (0.02% wt/wt; antioxidant). The corn oil solution (205 mg) was filled into size 0 two piece hard gelatin capsules.

Eight male Yucatan miniature swine per group were each administered a daily dose based on the dosing schedule in Table 9, below.

TABLE 9

| Group ID | Number/Gender of Animals | Dose Route | Dose/Animal |
|---|---|---|---|
| 1M | 8/male | Oral | 1 × 25 μg, immediate release 25-hydroxyvitamin $D_3$ capsule dosed daily for 21 days |
| 2M | 8/male | Oral | 1 × 25 μg, modified release 25-hydroxyvitamin $D_3$ capsule dosed daily for 21 days |
| 3M | 8/male | Oral | 1 × 125 μg, modified release 25-hydroxyvitamin $D_3$ capsule dosed daily for 21 days |

Blood was collected from animals prior to the first dose and daily at 24 h following daily dose, prior to subsequent dose. The concentration of serum 25-hydroxyvitamin $D_3$ was assayed using solid-phase extraction (SPE) with high performance liquid chromatography with tandem mass spectrometry (LC-MS/MS) detection. Total serum calcium was determined in samples collected from animals at the following time points: pre dose (Day 0) and 24 h following last dose (Day 21).

In all three groups, pre-dose mean serum 25-hydroxyvitamin $D_3$ concentrations were approximately 26 ng/mL. After 21 doses, an increase in serum 25-hydroxyvitamin $D_3$ was observed in all animals. Following the repeat administration of 25 μg MR or IR capsules, the concentration of serum 25-hydroxyvitamin $D_3$ increased to levels above 30 ng/mL and began to plateau at approximately 45 and 55 ng/mL, respectively at approximately Day 17 to 18. Upon the administration of a single dose, the increase in serum 25-hydroxyvitamin $D_3$ between the two regimens was comparable (3.84 versus 4.18 ng/mL). On the other hand, at the completion of dosing the increase was approximately 60% greater for animals administered the IR formulation. This finding indicates that the bioavailability from the MR capsule is comparable to that of the IR following a single dose, but that the MR capsules present a method for repeat dosing of 25-hydroxyvitamin $D_3$ in which systemic 25-hydroxyvitamin $D_3$ can be gradually increased.

Animals administered 125 μg MR capsules exhibited higher levels of serum 25-hydroxyvitamin $D_3$. The administration of a 5 fold greater dose (125 μg versus 25 μg MR capsules) resulted in approximately 5 fold greater increase in 25-hydroxyvitamin $D_3$ following single and repeated dose. This finding indicates that exposure from MR capsules is dose proportional from 25 to 125 μg.

The effect of the administration of IR and MR capsules on the concentration of serum calcium was investigated. After the administration of 21 doses of either IR or MR, the levels of calcium in serum did not change from pre-dose baseline levels. This finding indicates that 25-hydroxyvitamin $D_3$ MR capsules can be utilized to increase serum 25-hydroxyvitamin $D_3$ levels to above 100 ng/mL without causing an increase in serum calcium.

Figure 20:
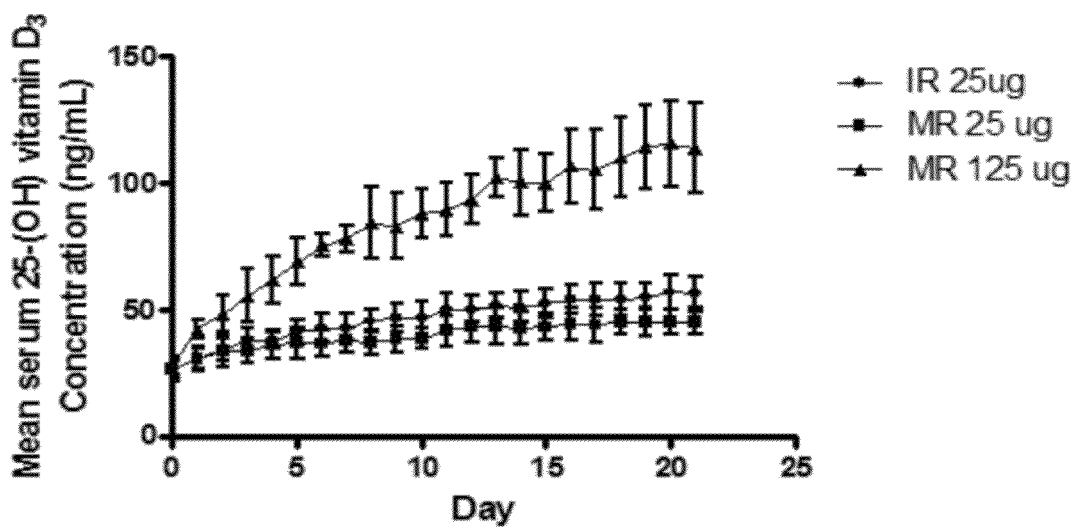
FIG. 20 shows mean uncorrected serum 25-hydroxyvitamin $D_3$ concentration versus time profiles for Groups 1 to 3 of miniature swine after administration of 25-hydroxyvitamin $D_3$ according to Example 3.
Figure 21:
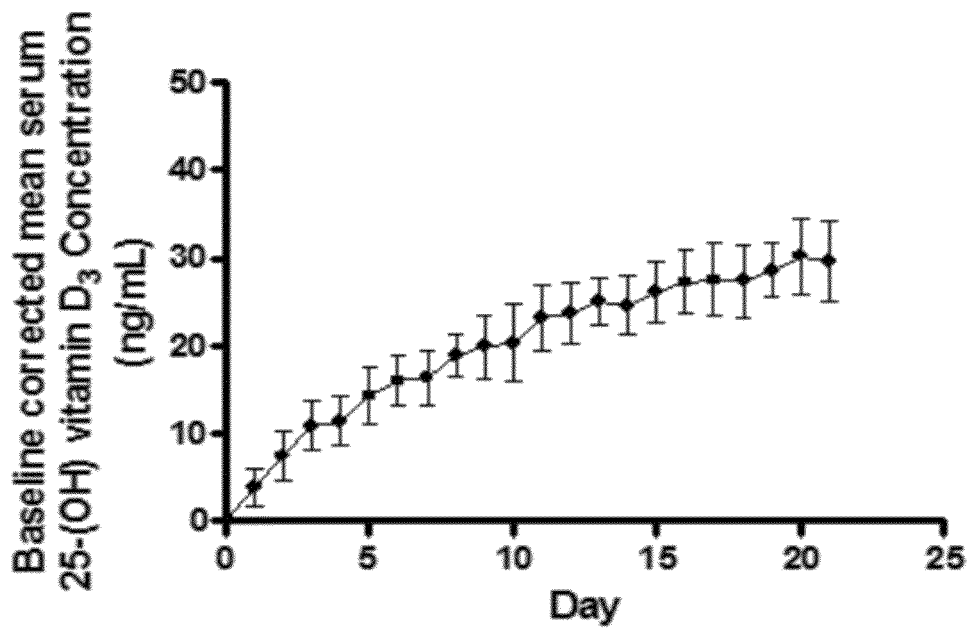
FIG. 21 through FIG. 23 show mean baseline corrected serum 25-hydroxyvitamin $D_3$ concentration versus time profiles for Groups 1 to 3 according to Example 3.
Figure 22:
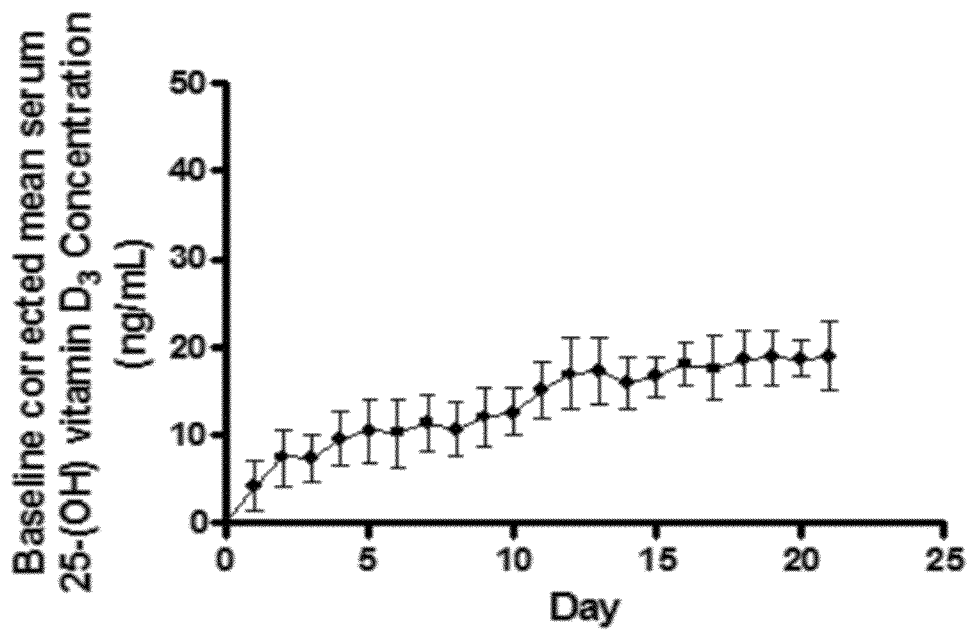
Figure 23:
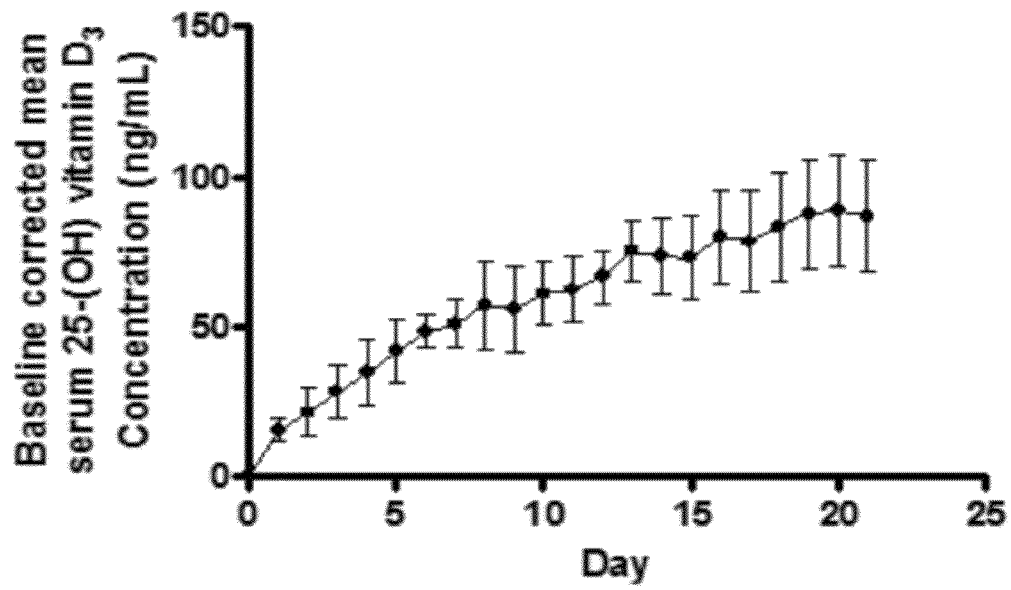

Mean uncorrected serum 25-hydroxyvitamin $D_3$ concentration versus time profiles for Groups 1 to 3 are illustrated in FIG. 20. Mean baseline corrected serum 25-hydroxyvitamin $D_3$ concentration versus time profiles for Groups 1 to 3 are illustrated in FIG. 21, FIG. 22, and FIG. 23, respectively.

Figure 24:
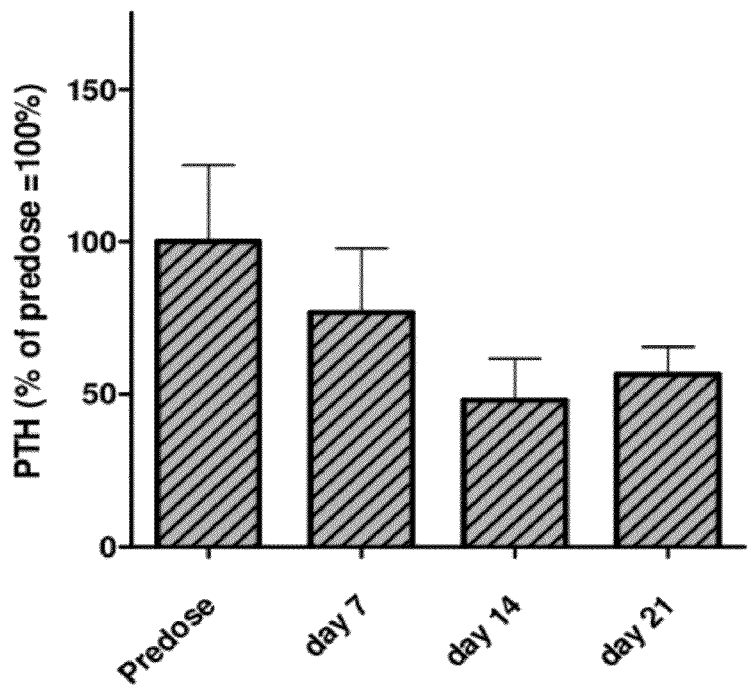
FIG. 24 shows the mean change in parathyroid hormone levels for Group 1 animals from predose to day 21.
Figure 25:
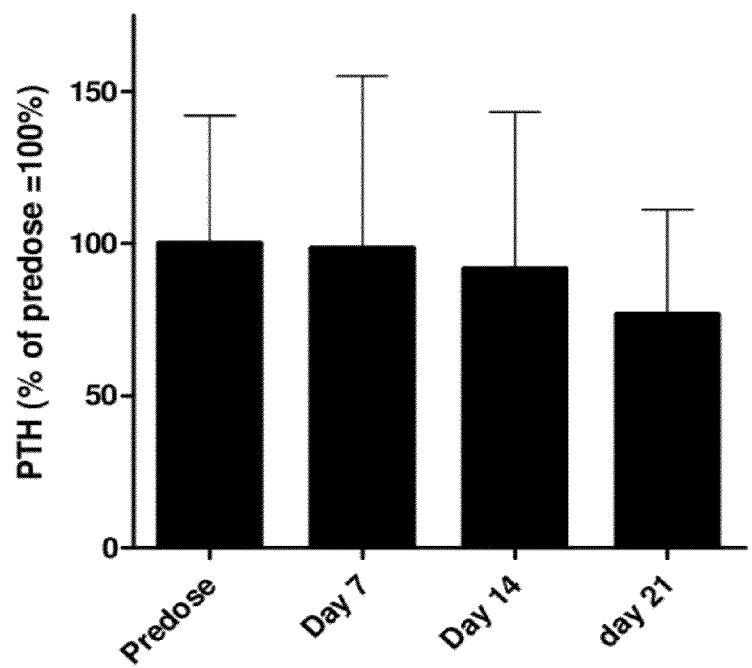
FIG. 25 shows the mean change in parathyroid hormone levels for Group 2 animals from predose to day 21, from Example 3.

FIG. 24 shows the mean change in parathyroid hormone levels for Group 1 animals from predose to day 21, and FIG. 25 shows the mean change in parathyroid hormone levels for Group 2 animals from predose to day 21. Immediate release and MR formulations both raise serum 25-hydroxyvitamin $D_3$; however, the immediate release formulation results in undesirable pharmacological decreases in PTH. The MR formulation does not effect acute supraphysiological reductions in PTH and allows for gradual PTH lowering, believed to be associated with physiological adaptation to markedly rising 25-hydroxyvitamin $D_3$ levels. The MR formulation should permit attainment of higher serum 25-hydroxyvitamin $D_3$ levels without safety concerns associated with undesirable pharmacological lowering of PTH.

Example 4

Pharmacokinetic Studies in Beagle Dogs with Oral Capsules

Modified release 25-hydroxyvitamin $D_3$ capsules were administered daily to Beagle dogs (10 kg) for 13 consecutive weeks. The MR formulations were prepared based on the formulation of Example 1, Group 7, above. The differences in concentration of 25-hydroxyvitamin $D_3$ were offset by relative changes in ethanol.

The capsules were administered orally, as shown in Table 10 below.

TABLE 10

| Treatment Group | Nominal Dose Level (μg/kg/day), based on 10 kg ave. weight | Dose/ Capsule (μg) | Number of Capsules |
|---|---|---|---|
| 1. Control Group (placebo) | 0 | 0 | 1 |
| 2. Low Dose | 2.5 | 25 | 1 |
| 3. Mid-Low Dose | 12.5 | 125 | 1 |
| 4. Mid-High Dose | 50 | 500 | 1 |
| 5. High Dose | 100 | 1000 | 1 |

Dogs were bled prior to the first dose and at specific time points following the first dose, up to 13 weeks (92 days). Serum was generated and 25-hydroxyvitamin $D_3$ was assayed in the serum using a liquid chromatography tandem mass spectrometry method.

Figure 26:
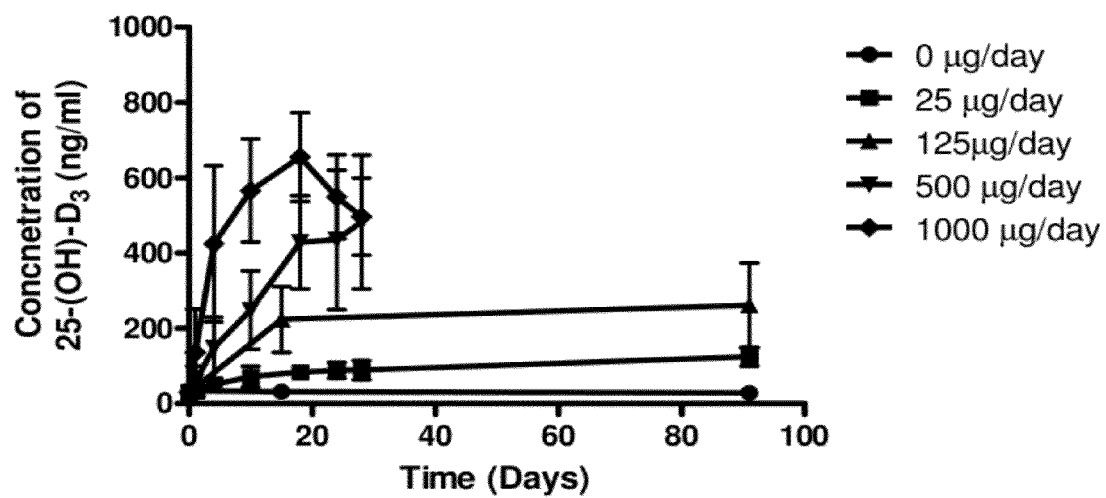
FIG. 26 shows mean serum 25-hydroxyvitamin $D_3$ concentration versus time profiles for Groups 1 to 5 of Beagle dogs administered 25-hydroxyvitamin $D_3$ modified release capsules according to Example 4.

Mean serum 25-hydroxyvitamin $D_3$ concentration versus time profiles for Groups 1 to 5 are illustrated in FIG. 26.

Example 5

Release Upon Dissolution

Figure 27:
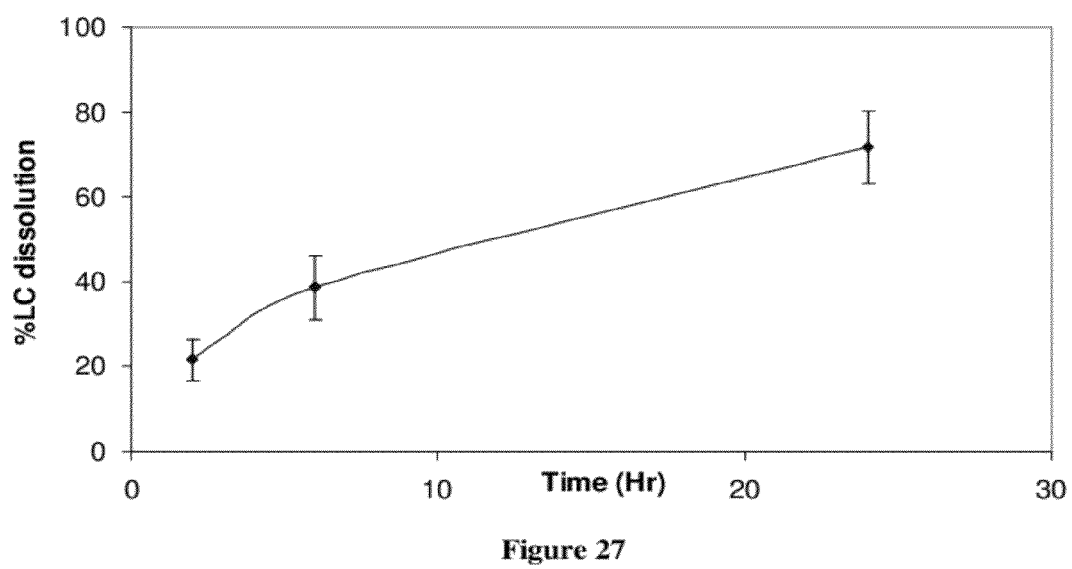
FIG. 27 shows a dissolution release profile for 250 µg capsules according to Example 2, which showed an average release of about 72% of 25-hydroxyvitamin $D_3$ at 24 hours.

FIG. 27 shows a dissolution release profile for 250 μg capsules according to Example 2 above, which showed an average release of about 72% of 25-hydroxyvitamin $D_3$ at 24 hours. As described above, preferably the modified release formulation releases about 80% of the drug in the first 24 hours.

Example 6

Efficacy Study in Healthy Adult Male Volunteers with Vitamin D Insufficiency

The effectiveness of three different formulations of Vitamin D in restoring serum 25-hydroxyvitamin D to optimal levels (>30 ng/mL) is examined in a 23-day study of healthy non-obese men diagnosed with Vitamin D insufficiency. One of the formulations (Formulation #1) is a soft gelatin capsule containing 30 μg of 25-hydroxyvitamin $D_3$ prepared as described in Example 1, Group 7, above. The second formulation (Formulation #2) is an immediate-release soft gelatin capsule of identical appearance containing 50,000 IU of ergocalciferol dissolved in medium chain triglyceride oil. The third formulation (Formulation #3) is an immediate-release soft gelatin capsule, also of identical appearance, containing 50,000 IU of cholecalciferol dissolved in medium chain triglyceride oil. A total of 100 healthy Caucasian and African-American men participate in this study, all of whom are aged 30 to 45 years and have serum 25-hydroxyvitamin D levels between 15 and 29 ng/mL (inclusive). All subjects abstain from taking other Vitamin D supplements for 60 days before study start and continuing through study termination, and from significant sun exposure. On Day 1 and 2 of the study, all subjects provide fasting morning blood samples to establish pre-treatment baseline values of serum 25-hydroxyvitamin D. On the morning of Day 3, the subjects provide an additional fasting blood sample (t=0), are randomly assigned to one of four treatment groups, and are dosed with a single test capsule prior to eating breakfast: the subjects in Group #1 each receive a single capsule of Formulation #1, and the subjects in Groups #2 and #3 each receive a single capsule of Formulation #2 or Formulation #3, respectively. Subjects in Group #4 receive a matching placebo capsule. Subjects in Group #1 each receive an additional capsule of Formulation #1 on the mornings of Days 4 through 22 before breakfast, but subjects in Groups #2, #3 and #4 receive no additional capsules. A fasting morning blood sample is drawn from each subject, irrespective of treatment group, on Days 4, 5, 6, 10, 17 and 23 (or 1, 2, 3, 7, 14 and 20 days after the start of dosing). All collected blood is analyzed for the contained levels of 25-hydroxyvitamin D, and the data are analyzed by treatment group after correction for baseline values. Subjects in all four treatment groups exhibit mean baseline serum 25-hydroxyvitamin D levels of approximately 16 to 18 ng/mL, based on analysis of fasting blood samples drawn on Days 1 through 3. Subjects in Group #4 (control group) show no significant changes in mean serum 25-hydroxyvitamin D over the course of the study. Subjects in Group #1 show a steadily increasing mean serum 25-hydroxyvitamin D reaching at least 30 ng/mL by Day 23. In marked contrast, subjects in Group #2 exhibit marked increases in mean serum 25-hydroxyvitamin D for the first few days post-dosing, reaching a maximum of 29 ng/ml and then rapidly declining thereafter. By study end, serum 25-hydroxyvitamin D is significantly lower than baseline in Group #2. Subjects in Group #3 exhibit continuing increases in mean serum 25-hydroxyvitamin D through the first 2 weeks after dosing with gradual, but progressive, decreases occurring thereafter. By study end, mean serum 25-hydroxyvitamin D is below 30 ng/mL, being only approximately 11 ng/mL higher than pre-treatment baseline. The data from this study demonstrate that administration of 600 μg of 25-hydroxyvitamin $D_3$, formulated as described herein and administered at a dose of 30 μg per day for 20 days, is substantially more effective in restoring low serum levels of 25-hydroxyvitamin D to optimal levels than immediate-release formulations of 50,000 IU of either ergocalciferol or cholecalciferol administered in single doses, as currently recommended by the NKF and other leading experts on oral Vitamin D replacement therapy.

Example 7

Efficacy Study in Patients with Stage 4 CKD and Secondary Hyperparathyroidism Associated with Vitamin D Insufficiency The effectiveness of oral immediate-release and modified-release 25-hydroxyvitamin $D_3$ in restoring serum total 25-hydroxyvitamin D to optimal levels (>30 ng/mL) and is examined in a 6-month study of adult male and female patients with Stage 4 CKD and secondary hyperparathyroidism associated with vitamin D insufficiency. Two formulations are used in the study. One of the formulations (Formulation #1) is a soft gelatin capsule containing 40 µg of 25-hydroxyvitamin $D_3$ in a modified-release formulation. The second formulation (Formulation #2) is a soft gelatin capsule containing 40 µg of 25-hydroxyvitamin $D_3$ in an immediate-release formulation. A total of 100 subjects participate in this study, all of whom are aged 30 to 70 years and have serum 25-hydroxyvitamin D levels between 15 and 29 ng/mL (inclusive) and serum intact parathyroid hormone (iPTH) levels above the target levels published in the current K/DOQI Guidelines at the time of enrolment. All subjects abstain from taking other Vitamin D supplements for 60 days before study start and continuing through study termination, and from significant sum exposure. All subjects begin daily dosing with two capsules of either Formulation #1 or Formulation #2. Serum total 25-hydroxyvitamin D is measured at biweekly intervals and serum iPTH is determined at quarterly intervals. After 1 month, the daily dosage of both Formulations is maintained unchanged in patients whose serum total 25-hydroxyvitamin D is between 50 and 90 ng/mL, increased by one capsule in patients whose serum total 25-hydroxyvitamin D is below 50 ng/mL, and decreased by one capsule per day in patients whose serum total 25-hydroxyvitamin D is above 90 ng/mL. Further adjustments in the daily dose are made in order to maintain serum total 25-hydroxyvitamin D between 50 and 90 ng/mL. Dosing with both Formulation #1 and #2 is continued indefinitely, provided that hypercalcemia, hypercalciuria and hyperphosphatemia do not develop, in which case appropriate adjustments in dosage are made. After 6-months, the subjects' serum total 25-hydroxyvitamin D levels are found to remain stable between 50 and 90 ng/mL with treatment with Formulation #1 and serum iPTH is found to remain stable at levels consistent with targets published in the K/DOQI Guidelines. The incidence of hypercalcemia, hypercalciuria and hyperphosphatemia are rare once stable dosing has been achieved. In contrast after 6-months, the subjects' serum total 25-hydroxyvitamin D levels are not found to remain stable between 50 and 90 ng/mL with treatment with Formulation #2 and serum iPTH does not reach levels consistent with targets published in the K/DOQI Guidelines. The incidence of hypercalcemia, hypercalciuria and hyperphosphatemia are substantial.

Data from this study demonstrate that the modified release formulation of 25-hydroxyvitamin $D_3$ is effective at increasing serum 25-hydroxyvitamin D without causing unacceptable side effects related to calcium and PTH metabolism.

The foregoing description is given for clearness of understanding only, and no unnecessary limitations should be understood therefrom, as modifications within the scope of the invention may be apparent to those having ordinary skill in the art.

Throughout the specification, where compositions are described as including components or materials, it is contemplated that the compositions can also consist essentially of, or consist of, any combination of the recited components or materials, unless described otherwise.

The practice of a method disclosed herein, and individual steps thereof, can be performed manually and/or with the aid of electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

What is claimed is:

1. A method of treating secondary hyperparathyroidism in Chronic Kidney Disease (CKD) Stage 3 or Stage 4 in a human patient, comprising administering to the patient an effective amount of a controlled release, oral dosage form of 25-hydroxyvitamin D to reduce the subject's serum parathyroid hormone level by at least 30% while safely raising serum total 25-hydroxyvitamin D.

2. The method of claim 1, wherein the subject is vitamin D insufficient or vitamin D deficient.

3. The method of claim 2, wherein said effective amount of the controlled release, oral dosage form of 25-hydroxyvitamin D is also effective to increase the subject's serum total 25-hydroxyvitamin D level to at least 30 ng/mL.

4. The method of claim 3, wherein said effective amount of the controlled release, oral dosage form of 25-hydroxyvitamin D is also effective to increase the subject's serum total 25-hydroxyvitamin D level to a value in a range of 50 ng/mL to 90 ng/mL.

5. The method of claim 1, wherein the subject's plasma intact parathyroid hormone level is reduced to the target range for the CKD Stage.

6. The method of claim 1, wherein the 25-hydroxyvitamin D is selected from the group consisting of 25-hydroxyvitamin D2, 25-hydroxyvitamin $D_3$, and a combination of 25-hydroxyvitamin $D_2$ and 25-hydroxyvitamin $D_3$.

7. The method of claim 6, wherein the 25-hydroxyvitamin D is 25-hydroxyvitamin $D_3$.

8. The method of claim 1, comprising administering said oral dosage on a schedule of once per day.

9. The method of claim 8, wherein the daily dose is in a range of 1 µg to 1000 µg.

10. The method of claim 1, wherein the daily dose of 25-hydroxyvitamin D is in a range of 1 µg to 1000 µg.

11. The method of claim 1, wherein the amount of 25-hydroxyvitamin D in the controlled release, oral dosage form is in a range of 1 µg to 1000 µg per unit dose.

* * * * *